(12) United States Patent
Davis

(10) Patent No.: US 10,004,866 B2
(45) Date of Patent: *Jun. 26, 2018

(54) FACIAL MASK APPARATUS AND METHOD OF MAKING

(71) Applicant: Lucy Carol Davis, Chapel Hill, NC (US)

(72) Inventor: Lucy Carol Davis, Chapel Hill, NC (US)

(73) Assignee: Lucy Carol Davis, Chapel Hill, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/710,417

(22) Filed: Sep. 20, 2017

(65) Prior Publication Data

US 2018/0028772 A1   Feb. 1, 2018

Related U.S. Application Data

(63) Continuation-in-part of application No. 13/835,059, filed on Mar. 15, 2013.

(51) Int. Cl.
  *A61M 16/06*  (2006.01)
  *A61B 5/00*   (2006.01)
  *A62B 18/02*  (2006.01)

(52) U.S. Cl.
  CPC ....... *A61M 16/0616* (2014.02); *A61B 5/4818* (2013.01); *A61M 16/06* (2013.01); *A61M 16/0644* (2014.02); *A61M 16/0683* (2013.01); *A61M 2016/0661* (2013.01); *A61M 2207/00* (2013.01); *A62B 18/02* (2013.01)

(58) Field of Classification Search
  CPC ................. A61M 16/06; A61M 2016/0661
  See application file for complete search history.

(56) References Cited

U.S. PATENT DOCUMENTS

| | | | |
|---|---|---|---|
| 2,671,445 | A | 3/1954 | Charbonnel |
| 4,985,116 | A | 1/1991 | Mettler et al. |
| 4,989,596 | A | 2/1991 | Macris et al. |
| 5,280,305 | A | 1/1994 | Monroe et al. |
| 5,492,116 | A | 2/1996 | Scarberry et al. |
| 6,148,817 | A | 11/2000 | Bryant et al. |
| 6,543,450 | B1 | 4/2003 | Flynn |
| 7,827,038 | B2 | 11/2010 | Richard et al. |
| 8,020,276 | B2 | 9/2011 | Thornton |
| 8,254,637 | B2 | 8/2012 | Abourizk et al. |
| 8,573,217 | B2 | 11/2013 | Todd et al. |
| 9,149,593 | B2 | 10/2015 | Dravitzki et al. |
| 2004/0263863 | A1 | 12/2004 | Rogers et al. |
| 2005/0016544 | A1 | 1/2005 | Thornton |
| 2006/0005837 | A1 | 1/2006 | Thornton |
| 2006/0023228 | A1 | 2/2006 | Geng |
| 2006/0058632 | A1 | 3/2006 | McBurnett et al. |
| 2008/0060648 | A1 | 3/2008 | Thornton et al. |

(Continued)

FOREIGN PATENT DOCUMENTS

| | | |
|---|---|---|
| WO | 2000035525 A1 | 6/2000 |
| WO | 2011049548 A1 | 4/2011 |
| WO | 2013026091 A1 | 2/2013 |

*Primary Examiner* — LaToya M Louis
(74) *Attorney, Agent, or Firm* — NEO IP

(57) ABSTRACT

A face mask for extended wear by a user including a customized, contoured facial mask portion constructed and configured to cover and matingly contact a corresponding contoured surface area of a human face, preferably formed by 3D printing methods and materials.

18 Claims, 22 Drawing Sheets

(56) References Cited

U.S. PATENT DOCUMENTS

| | | |
|---|---|---|
| 2008/0060652 A1 | 3/2008 | Selvarajan et al. |
| 2009/0084384 A1 | 4/2009 | Cheng et al. |
| 2009/0107501 A1 | 4/2009 | Krieger |
| 2009/0266362 A1 | 10/2009 | Mark |
| 2010/0199992 A1 | 8/2010 | Ho et al. |
| 2010/0258133 A1 | 10/2010 | Todd et al. |
| 2011/0220112 A1 | 9/2011 | Connor |
| 2011/0240030 A1 | 10/2011 | Ho et al. |
| 2011/0247628 A1 | 10/2011 | Ho |
| 2012/0180794 A1 | 7/2012 | Smart |
| 2012/0305003 A1 | 12/2012 | Mark |
| 2012/0318272 A1 | 12/2012 | Ho et al. |
| 2013/0068230 A1 | 3/2013 | Jablonski |
| 2014/0000615 A1 | 1/2014 | Wanderer |
| 2014/0034058 A1 | 2/2014 | Lang et al. |

FACIAL MASK APPARATUS AND METHOD OF MAKING

CROSS REFERENCE TO RELATED APPLICATIONS

This application is related to and claims priority from the following U.S. patents and patent applications. This application is a continuation-in-part of U.S. application Ser. No. 13/835,059 filed Mar. 15, 2013, which is incorporated herein by reference in its entirety.

BACKGROUND OF THE INVENTION

1. Field of the Invention

The present invention relates to a face mask apparatus, and more particularly, to a face mask apparatus for sleep apnea treatment, and methods of making same.

2. Description of the Prior Art

Sleep apnea is a condition characterized by pauses in breathing or shallow breaths while sleeping. The pauses in breathing may last for a few seconds to a few minutes, and may occur more than 30 times an hour. Left untreated, sleep apnea leads to excessive daytime sleepiness and an increased risk of high blood pressure, heart attack, stroke, obesity, diabetes, and heart failure.

Treatment options for sleep apnea generally include lifestyle changes (e.g., weight loss, avoiding sleeping on one's back, avoiding alcohol, smoking cessation), surgery, mouth pieces, and breathing devices. The most common treatment for sleep apnea is a continuous positive airway pressure (CPAP) or automatic positive airway pressure (APAP) device. These devices blow pressurized air via a hose to a nasal pillow, nose mask, or facial mask at a pressure high enough to splint the airway open during sleep.

It is known in the prior art to provide sleep apnea treatment medical devices. Currently, masks are made from plastic, and are adjusted by either foam or gel to suit the comfort level of the patient. In addition, the gel or foam is also utilized to form the seal between the mask and the patient's skin. The seal is an important part of the effectiveness of the mask because it ensures that air does not leak out.

It is also known in the art to provide customizable masks for facial application. It is further known in the art to use computer aided design for custom face mask design and manufacture. And it is also known to provide three-dimensional (3D) facial data for use for fabrication of a custom fit mask for medical procedures.

Examples of relevant prior art reference documents include the following:

U.S. Publication No. 20120305003 for "Rapid Production Of Customized Masks" by inventor Mark, filed Oct. 21, 2009 and published Dec. 6, 2012, is directed to a system designed for the rapid preparation of anatomically customized mask employing data from a patient. The data may take the form of a multidimensional image of a target area of a patient's face obtained by optical 3 dimensional imaging, or a dot or line scan form laser imaging, pattern laser photography or stereo photography. Also disclosed is a mask that is made of a thin layer, so it is lightweight and closely hugs the targeted region upon which it rests (e.g. the nasal region). The body of the mask is made of a thin layer, so it is lightweight and closely hugs the targeted region upon which it rests (e.g. the nasal region). Methods for producing anatomically customized masks are also described.

U.S. Pat. No. 5,280,305 for "Method and apparatus for forming a stylized, three-dimensional object" by inventors Monroe et al., filed Oct. 30, 1992 and issued Jan. 18, 1994, is directed to a device that produces a three-dimensional object with custom art work from an electronic signal. More particularly, the preferred implementation is a device for making masquerade-type masks, and includes a digital camera that captures a front-on image of an individual's face and converts the captured image to an electronic signal that is downloaded into a personal computer. The computer is utilized to select an image, process that image to remove background, scale the image to correspond to the dimensions and features of a facial die that will be used to mold the mask, and to provide for special effects processing of the selected image. An inkjet plotter is then directed to print the processed image upon thin, flat plastic, which is aligned with the facial features of the die and deformed to skin tight conformance with the die by a vacuum-forming process. The finished mask bears art work, upon its convex exterior, that realistically imitates the face of the individual which served as the model for the mask.

U.S. Pat. No. 4,985,116 for "Three dimensional plating or etching process and masks therefor" by inventors Mettler et al., filed Feb. 23, 1990 and issued Jan. 15, 1991, is directed to a process for plating or etching metalization patterns on the surface of a three dimensional substrate, wherein a flexible plastic mask is fabricated by first coating the surface of a thin plastic sheet with vacuum formable ink. The mask is then molded into the shape of the surface into which the pattern is to be formed. A low power YAG laser is used to remove areas of the ink through which light is to be allowed to pass. This mask may then be used in either a print and plate process or a print and etch process by drawing the mask into intimate contact with the workpiece by applying a vacuum between the mask and the workpiece. The workpiece may then be exposed to light through the clear areas of the mask.

U.S. Pat. No. 8,020,276 for "System and method for custom-orienting a medical mask to an oral appliance" by inventor Thornton, filed Nov. 29, 2007 and issued Nov. 20, 2011, is directed a medical mask including a body and an orientation structure. The body includes a first polymer, is configured to cover portions of a user's face comprising the user's mouth and at least portions of the user's nose comprising the nostrils, and is further configured to contact the user's face surrounding the covered portions of the user's face to substantially prevent gas from escaping between the body and the contacted portions of the user's face. The orientation structure is configured to receive an oral appliance post to establish and maintain a custom orientation between the medical mask and the oral appliance post and the orientation structure includes a deformable material which includes a second polymer capable of transitioning between deformable and non-deformable states.

U.S. Pat. No. 8,254,637 for "Mask fitting system and method" by inventors Abourizk et al., filed Jul. 26, 2007 and issued Aug. 28, 2012, is directed a system and methods for selecting a mask system for a patient, where certain example embodiments include generating 3D contours of patients and selecting mask systems based at least on those contours. These contours may be generated by using, for example, a cushion of translatable pins, a nasal cannular scanning device, and/or a shadow stereopsis sensor. Certain other example embodiments allow images and/or videos to be captured and optionally synchronized. Then, images of various mask systems may be overlaid to determine how well a mask system fits. In still other embodiments, a user can hold a transparency corresponding to a mask design in front of the patient's face to determine how well a mask system fits.

U.S. Pat. No. 7,827,038 for "Mask fitting system and method" by inventors Richard et al., filed Jun. 6, 2005 and issued Nov. 2, 2010, is directed to a mask fitting system for selecting a mask system for a patient includes at least one terminal which receives data unique to a patient. The patient data can be scanned in using a scanner, such as a handheld or 3-D scanner, or the relevant dimensions of the patient can be simply input into the terminal. A database is provided to store mask system data relating to a plurality of potential mask system solutions for the patient. A communication channel is provided by which the data received by the terminal can be compared with mask system data stored in a mask system database, so as to generate a best-fit mask system result. The best-fit result may include one or more mask system recommendations for the patient.

U.S. Publication No. 20060023228 for "Custom fit facial, nasal, and nostril masks" by inventor Geng, filed Jun. 10, 2005 and issued Feb. 2, 2006, is directed to a process for fabricating a facial mask to custom fit a patient's face for a comfortable fit for facilitating various medical procedures including the steps of generating a 3D data set to define a portion of a patient's face to be fitted with a custom mask, fabricating a patient's mask utilizing a patient's 3D facial data set, and fitting a patient with a custom fit facial mask for facilitating a desired medical procedure.

U.S. Publication No. 20040263863 for "System and method for design and manufacture of custom face masks" by inventors Rogers et al., filed Jan. 27, 2004 and issued Dec. 30, 2004, is directed to methods and systems for forming face masks. Embodiments may utilize computer-aided design and computer-aided manufacturing to form custom fitted face masks. System software may be configured to acquire facial topography information, design a mask based on the topography information, and send mask information to a computerized manufacturing device. The software may communicate with a scanning device for facial topography acquisition and a milling machine for pattern fabrication. In an embodiment, the scanning device may include a linear scan non-contact laser imager. In an embodiment, the scanning device may be manually moved with respect to an individual being scanned, thereby eliminating the need for motive apparatus. In such embodiments, position information may be determined based on data from a position sensor coupled to the scanning device.

U.S. Publication No. 20100199992 for "Cushion inside a cushion patient interface" by inventors Ho et al., filed Apr. 27, 2010 and published Aug. 12, 2010, is directed to a patient interface device that includes a mask shell and a cushion assembly. The cushion assembly includes a seal cushion and a support cushion. The seal cushion contacts a first area of a patient's face to form a seal therewith. The support cushion defines a second area over a face of such a patient when the patient interface device is being worn. The second area overlaps at least a portion of the first area.

U.S. Patent No. 20100258133 for "Face mask" by inventors Todd et al., filed Nov. 11, 2008 and published Oct. 14, 2010, is directed to a mask assembly for delivering gas to a patient that includes a mask body and a breathing circuit interface. The mask body includes an opening for reception of the gas and includes a seal structure for sealingly engaging with the face of the patient and surrounding at least the nose and mouth of the patient. The breathing circuit interface includes a first portion rotatably connected with the mask body and a second portion that is constructed and arranged to releasably connect with a conduit for delivering the gas to the patient through the opening.

U.S. Publication No. 20080060648 for "Stability Medical Mask" by inventors Thornton et al., filed Sep. 11, 2007 and published Mar. 13, 2008, is directed to a medical mask including a rigid sealing portion configured to cover and seal around at least a portion of a user's nose including the user's nostrils and a rigid stabilizing frame coupled to the rigid sealing portion. The rigid stabilizing frame includes a generally horizontal upper support member configured to bear against the user's forehead, a generally vertical support member coupled between the rigid sealing portion and the upper support member, and lower left and right support members coupled between the rigid sealing portion and the upper support member and configured to bear against the user's cheeks. The rigid stabilizing frame defines two openings configured to allow the user to see through the medical mask when the medical mask is positioned on the user's face.

WIPO Publication No. WO2013026091 for "Manufactured to shape headgear and masks" by inventors Dunn et al., filed Aug. 21, 2012 and published Feb. 28, 2013, is directed to a headgear or headgear segments that are manufactured to shape thereby producing little or no waste material. Techniques such as knitting, braiding, crocheting, and 3D printing can be used produce the headgear.

U.S. Pat. No. 5,492,116 for "Respiratory mask with floating seal responsive to pressurized gas" by inventors Scarberry et al., filed Jun. 3, 1994 and issued Feb. 20, 1996, is directed to a respiratory mask adapted to confront the face of a user in a manner to float with respect to the user's face on a cushion of gaseous medium contained within the mask for user breathing, the gaseous medium being contained within the mask by a flexible seal means carried by the mask and maintained in sealing engagement with the user's face while providing essentially no structural support for the mask with respect to the user's face.

SUMMARY OF THE INVENTION

The present invention relates to extended wear contoured facial masks.

It is an object of this invention to provide a customized, contoured facial mask constructed and configured to cover and to contact a corresponding contoured surface area covering a substantial surface area of a human face.

A further object of this invention is to provide methods of making the customized, contoured facial mask using three dimensional (3D) printing methods and materials.

Accordingly, a broad embodiment of this invention is directed to customized, contoured facial masks for sleep apnea treatment.

In one embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the facial mask is configured to not cover and not contact eyes of the individual user during use, and wherein the at least one strap is sized to extend around the user's head and is for applying a pressure distributed across the customized, contoured facial mask portion.

In another embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the customized, contoured facial mask portion is sized to matingly contact at least 50% of the surface area of the face of the individual user, and wherein the at least one strap is sized to extend around the user's head and is for applying a pressure distributed across the customized, contoured facial mask portion.

In yet another embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the contact portion is adapted to contact supraorbital ridges of the individual user during use, wherein the customized, contoured facial mask portion is sized to matingly contact at least 80% of the surface area of the face of the individual user, and wherein the at least one strap is sized to extend around the user's head and is for applying a pressure distributed across the customized, contoured facial mask portion.

These and other aspects of the present invention will become apparent to those skilled in the art after a reading of the following description of the preferred embodiment when considered with the drawings, as they support the claimed invention.

DETAILED DESCRIPTION

Figure 1:
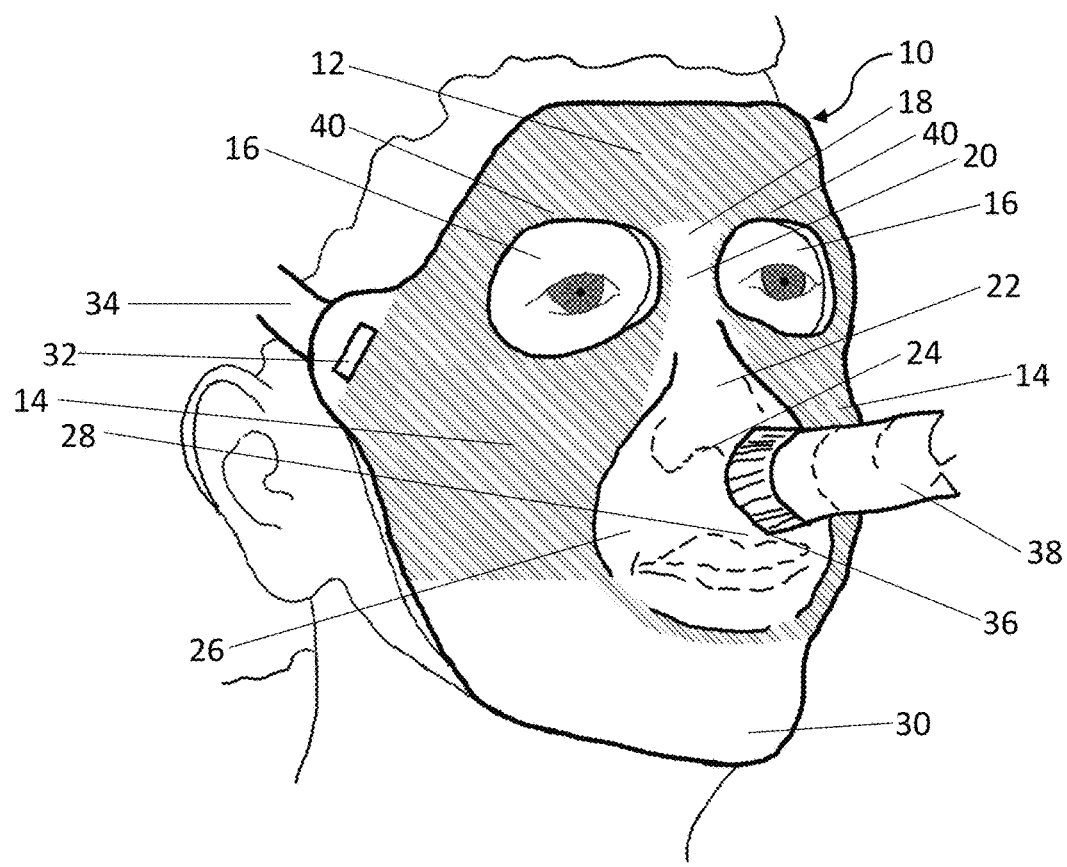
FIG. 1 is a schematic diagram of a perspective view of one embodiment of the invention.

The present invention is generally directed to a face mask apparatus, and more particularly, to a face mask apparatus for sleep apnea treatment, and methods of making the same.

In one embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the facial mask is configured to not cover and not contact eyes of the individual user during use, and wherein the at least one strap is sized to extend around the user's head and is for applying a pressure distributed across the customized, contoured facial mask portion.

In another embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the customized, contoured facial mask portion is sized to matingly contact at least 50% of the surface area of the face of the individual user, and wherein the at least one strap is sized to extend around the user's head and is for applying a pressure distributed across the customized, contoured facial mask portion.

In yet another embodiment, the present invention provides a facial mask for addressing sleep apnea in an individual user, including a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use, wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user, wherein the customized, contoured facial mask portion is adapted to extend below a chin of the individual user during use, wherein the contact portion is configured to not contact a chin boss of the individual user during use, wherein the contact portion is configured to not contact a nose of the individual user during use, wherein the contact portion is configured to not contact a philtrum of the individual user during use, wherein the contact portion is configured to not contact a glabella of the individual user during use, wherein the contact portion is adapted to substantially contact a forehead of the individual user during use, wherein the contact portion is adapted to substantially contact cheeks of the individual user during use, wherein the contact portion is adapted to contact supraorbital ridges of the individual user during use, wherein the customized, contoured facial mask portion is sized to matingly contact at least 80% of the surface area of the face of the individual user, and wherein the at least one strap is sized to extend around the user's head and is for applying a pressure distributed across the customized, contoured facial mask portion.

As previously described, sleep apnea is a disorder characterized by abnormal breathing during sleep. The abnormality can range from shallow breathing to pauses in breathing while sleeping. If left undiagnosed, other medical conditions may ensue, such as high blood pressure, heart attack, stroke, obesity, diabetes, and heart failure. The disorder is diagnosable by a sleep study conducted in a monitored facility. Sleep apnea symptoms include snoring while sleeping, fatigue during the day, and sleepiness during the daytime hours. The treatments for sleep apnea are: surgery, lifestyle changes (e.g., weight loss, avoiding sleeping on one's back, avoiding alcohol, smoking cessation), mouth pieces, and breathing devices. Breathing devices are the most common form of treatment for sleep apnea patients. The device uses a full facial mask, a mask that fits over the nose and mouth, or a nasal mask. The mask is then connected to a machine that blows small amounts of air into the airway to ensure the airway remains open while sleeping. The machine is oftentimes referred to as a Continuous Positive Airway Pressure (CPAP), Automatic Positive Airway Pressure (APAP), or a Bi-level Positive Airway Pressure (BiPAP) device. The mask used with these devices are important, as masks that are not adjusted correctly can result in irritation, bloating, dry mouth and nose, and other problems.

Masks often come in standardized sizes (e.g., small, medium, large). Additionally, there are different masks for males, females, children, and infants. However, they are typically not customized and create impressions and indentations on the face of the user during and/or after use. As the mask must be worn all night, every night, these impressions and indentations on the face of the user may become permanent. Further, many users have to try out multiple masks in order to find one that is comfortable and fits properly, which causes frustration and can be very expensive.

It is difficult to find a mask with a good fit because facial dimensions and contours are unique to each person. In a 2014 study conducted by Sheehan and Nachman published in *Nature Communications*, the researchers used a database of body measurements compiled from male and female military personnel in 1988 to evaluate the variability in human facial features based on sixteen different facial measurements. The researchers concluded that each individual facial trait is independent of other facial traits, unlike traits of other parts of the body. For example, while the length and width of an individual's hand are correlated, such that a person with a long hand would also be expected to have a wide hand, the length and width of the nose are not correlated. Further, the largest amount of variability with facial traits are within the triangle of the eyes, mouth, and nose. Sleep apnea masks are concerned with this triangle, which is why it is so difficult to find a mask that fits properly.

Because the mask often does not fit properly, users may tighten the straps of the mask too much to obtain a seal, causing pain and discomfort. Further, the mask often causes creases, lines, or other undesired cosmetic changes in the user's face due to extended use of the mask. Most prior art masks are configured for perimeter contact of the mask with the face (e.g., around the entire face or around the nose and mouth). The pressure of the mask caused by the straps holding the mask to the face of the user is distributed only across the perimeter contact portion. Wearing a mask with only this perimeter contact causes creases or lines in the face of the user. Other masks (e.g., nasal masks) may exert pressure on the nasolabial folds, glabella, or other areas prone to wrinkles. Further, other masks have one or more straps that contact the cheeks or forehead, which may lead to creases, lines, and other cosmetic changes in the user's face.

What is needed is a facial mask to address sleep apnea that can be used all night, every night, that is comfortable, provides a custom fit for the user, and does not cause lines, wrinkles, and other undesired cosmetic changes in the user's face. There is a long-felt unmet need for a facial mask that prevents undesired cosmetic changes in the user's face due to extended wear of the mask, provides for increased comfort by contacting a large surface area of the face while not contacting the glabella, the philtrum, the nose or the chin boss of the user, requires only one strap to hold the mask to the user's face, and does not cover and does not contact the eyes of the individual user.

None of the prior art discloses a facial mask that matingly contacts at least 50% of the surface area of the face and matches the facial contours of the individual user, does not cover and does not contact the eyes during use, does not cause undesired cosmetic changes in the user's face, and does not contact the glabella, the nose, the nasolabial folds, the philtrum, and the chin boss of the user. Advantageously, the facial mask of the present invention can be secured to the user's face with a single strap due to the large surface area of the face (i.e., at least 50% of the surface area) in mating contact with the facial mask. Preferably, mating contact or "matingly" as used in this application means that two components are formed of mutually complementing shapes that physically connect. Examples of mating connections include electrical connectors, jigsaw puzzles, and a bolted joint. One of the most common examples of a mating connection is a bolt, which has external threads, and a nut, which has internal threads. In this example, the bolt acts as a "male" component, while the nut acts as a "female" component. Mating components maintain their entire physical integrity when in contact with each other. Neither component becomes deformed when in contact with the other.

Referring now to the drawings in general, the illustrations are for the purpose of describing a preferred embodiment of the invention and are not intended to limit the invention thereto.

The present invention provides a three-dimensional (3D) printed custom face mask component of a sleep apnea treatment device, which addresses the need for customizable masks connected to the machine. The present invention utilizes 3D printing technology to create customizable masks for sleep apnea patients.

The present invention provides a customized sleep apnea mask formed utilizing 3D printing technologies that conforms to the unique facial features of an individual user. The mask embodiments of the present invention are customizable for each user to provide matching contours of the human face for increased comfort when the mask is worn.

In one embodiment of the present invention a 3D model of the anatomically customized mask is created using multidimensional data of an individual's face. The multidimensional data of the individual's face may be acquired through the use of 3D scanners, multiple image or video cameras and digital reconstruction software, dot or line scans from laser imaging, pattern laser photography, stereo photography, or any number of 3D modeling technologies. In one embodiment, the multidimensional data of the individual's face is acquired while the individual is lying down. Once digitization of the face's 3D surface occurs, an operator may further customize the mask to provide enhanced functionally and aesthetics. For example, and not by way of limitation, the operator may use a computer aided design (CAD) or modeling software to define the boundaries of the mask, create modifications such as strap attachment slit or airway passage, or allow for modular connections such as for a breathing tube.

In another embodiment, the multidimensional data of the individual's face is obtained using a smartphone or a tablet.

The multidimensional data of the individual's face is acquired through multiple images and/or video taken with the smartphone or the tablet. In one embodiment, the smartphone or the tablet utilizes an accelerometer or other sensors to ensure that sufficient data is acquired. In another embodiment, the smartphone or the tablet has a mobile application that is operable to transmit the multidimensional data of the individual's face to the operator. The mobile application is also operable to allow the individual to request modifications and features to customize the facial mask.

Since 3D printing in additive printing embodiments involves printing in layers, any digitized model must be mathematically translated, usually by the printer software, into cross-sections or "slices" of the desired print-out. Any intermediate or finalized 3D digital model (e.g., a STL, VRML, or AMF file) may be read by the 3D printer for creating the cross-sections or "slices." Additionally, the model is analyzed by the printer software in order to determine the most structurally efficient location to print extraneous supports to aid in the printing process. These supports are operable to be removed through chemical or manual removal techniques following printing.

In another embodiment, subtractive manufacturing is used in order to remove material from a starting material or block. In this case, standard mathematical operations are performed by the 3D printer to determine the appropriate angle, strength, and depth with which to remove material from the starting material or block. This process is completed on a subtractive 3D printer (e.g., a CNC machine). In a preferred embodiment, the subtractive 3D printer is operable to cut around at least three axes. Advantageously, this minimizes the number of times the starting material or block must be turned during the printing process. In one embodiment, a combination of additive and subtractive printing methods is used to manufacture the face mask.

In yet another embodiment, more advanced methods of 3D are used, such as laser-based stereolithography (SLA), digital light processing (DLP), or other resin-based printing methods, such as continuous liquid interface production (CLIP). The resin-based methods provide the benefit of more customizable, faster printing, while allowing for variability in material choice.

Furthermore, the present invention allows for 3D modeling data to be stored in a database for future use. Such a database, housed in a non-transitory medium such as the memory of a computer, can contain modeling data for individual face contours, modifications to these contours, templates for enhanced functionality or aesthetics, or 3D models of objects to be incorporated into or on to a facial mask. The database of modeling data can be used to reproduce previously printed 3D masks or can be used to adapt such data to a future use, including inventory management, record-keeping, or branding. In one embodiment, the database is accessible through a web interface, providing access to operators, customers, or third parties, with granted access to the database capable of being limited. In one embodiment, the database is accessible through a mobile application on a smartphone.

Importantly, to ensure customized fit of the face mask, the contact portion of the customized, contoured facial mask is constructed and configured to cover and to matingly contact a corresponding contoured surface area of a human face, is unitarily and integrally formed by 3D printing, and is formed of a synthetic material or plastic. Preferably, a flexible layer is provided on the surface that contacts the face of the user, i.e., that contacts and "mates" with the contours of the user's face, for additional comfort increase. In one embodiment, the flexible layer is a soft plastic layer, a silicone layer, or a rubber layer. So then both the coverage of the mask over the face of the user and the soft underside layer each separately and in combination provide maximum pressure distribution over the face surface of the user. Thus, the face mask may be formed of a stratified, multilayer structure, wherein the underside layer that contacts the user's face is a softer material than the outer layer, although the layers may be formed integrally together or bonded together. A stratified, multilayer mask refers to a mask formed or deposited in individual layers, wherein one layer is over or under at least one other layer (i.e., like stratified rock formations in geology). In a preferred embodiment, the underside layer is a flexible layer and the outer layer is a rigid layer. The rigid outer layer provides structural support for the face mask, while the flexible underside layer provides comfort to the user.

U.S. Pat. Nos. 5,869,170, 7,565,633, 7,845,352, 7,963,284, 8,147,910 and 8,175,734, U.S. Publication No. 20120224755, and European Patents 2486547 and 2482248 are hereby incorporated by reference in their entirety. These documents describe details of 3D printing, materials used for 3D printing, and customizable masks made of plastic or gel materials including but not limited to plastic, living cells, leather, nylon, metal, and thermoplastics.

U.S. Publication No. 20120305003 for "Rapid Production Of Customized Masks" by inventor Mark, filed Oct. 21, 2009 and published Dec. 6, 2012, is hereby incorporated by reference in its entirety. This application describes a system designed for the rapid preparation of anatomically customized mask employing data from a patient. The data may take the form of a multidimensional image of a target area of a patient's face obtained by optical 3-dimensional imaging, or a dot or line scan form laser imaging, pattern laser photography or stereo photography. Also disclosed is a mask that is made of a thin layer, so it is lightweight and closely hugs the targeted region upon which it rests (e.g., the nasal region).

FIG. 1 is a schematic diagram of a perspective view of one embodiment of the invention. The contact area is depicted in FIG. 1 by the shaded region. In a preferred embodiment, the contact area of the facial mask 10 includes the forehead 12 and the cheeks 14. The forehead 12 is the skin under the hairline and above the eyebrows and ears. Preferably, the mask is configured to cover and matingly contact about 90% of the forehead during use. In other embodiments, the mask is configured to cover and matingly contact about 100% of the forehead during use, about 95% of the forehead during use, about 85% of the forehead during use, about 80% of the forehead during use, about 75% of the forehead during use, or about 70% of the forehead during use. The cheeks 14 are on either side of the face below the eye and above the jaw. The cheeks 14 are by surface area the largest subunit of the face. Preferably, the mask is configured to cover and matingly contact about 90% of the cheeks during use. In other embodiments, the mask is configured to cover and matingly contact about 100% of the cheeks during use, about 80% of the cheeks during use, about 70% of the cheeks during use, about 60% of the cheeks during use, about 55% of the cheeks during use, or about 50% of the cheeks during use. In one embodiment, the contact area includes the brow ridges (supraorbital ridges) 40.

In a preferred embodiment, the facial mask 10 does not cover and does not contact the eyes of the user. As shown in FIG. 1, the facial mask 10 preferably includes two openings 16 for the user's eyes when the facial mask 10 is on the face of the user. The mask is thus preferably in mating contact with the skin which surrounds the eyes of the user. Full face masks can fog up or become dirty and block the user's vision. Additionally, full face masks lead to dry eyes and other eye issues for patients. The present invention advantageously does not cover and does not contact the eyes, which provides comfort to the user and prevents the eyes from drying out. Further, air leakage from nasal masks can also cause the eyes to dry out. This air leakage is often caused by a mask with a poor fit. Advantageously, the present invention provides the user with a custom fit facial mask that mates with the contours of the user's face, providing a good fit and preventing air leakage that can cause the eyes to dry out. There is a longfelt, unmet need in the art for a sleep apnea mask which is operable to minimize or eliminate cosmetic changes typically caused by extended wear of the mask while simultaneously providing the benefit of preventing air leakage that causes the user's eyes to dry out.

The facial mask preferably does not contact the glabella 18, the root of the nose 20, the nose 22, the nostrils 24, the philtrum 28, and the chin boss 30 of the user. These areas of the face are more sensitive than other areas of the face and may cause discomfort to the user if contacted by the mask. In another embodiment, the facial mask does not contact the nasolabial folds (i.e., "smile lines" or "laugh lines") 26. Some of these areas (e.g., the glabella 18, the nasolabial folds 26, and the philtrum 28) are prone to wrinkles. Advantageously, not contacting the face in these areas helps to prevent lines, creases, or other undesired cosmetic changes in the user's face with continued of the facial mask.

The present invention differs from the prior art, including U.S. Publication Nos. 20120305003 and 20100258133, in that it is designed to minimize the cosmetic changes to the face of the user upon continual use of the mask. The present invention does this by providing a much larger contact area than the prior art, including the large surfaces areas of the face, such as the forehead 12 and the cheeks 14. The term "face" is understood by one of ordinary skill in the art. By way of illustration and not limitation, the term "face" refers to the front portion of the head, defined vertically from the top of the forehead to the base of the chin and horizontally from the start of each ear. The face thus includes, inter alia, the forehead, the eyes, the nose, the mouth, the cheeks, the jaw, the glabella, the superciliary arches, the philtrum, the superior palpebral sulcus, the inferior palpebral sulcus, the palpebromalar sulcus, nasolabial folds, mentolabial sulcus, and any other features that are located vertically between the top of the forehead and the base of the chin and horizontally between the start of each ear. In a preferred embodiment, the facial mask covers and matingly contacts at least 80% of the surface area of the face of the user. In another embodiment, the facial mask covers and matingly contacts at least 50% of the surface area of the face of the user. Alternatively, the facial mask covers and matingly contacts at least 60% of the surface area of the face or at least 70% of the surface area of the face of the user. In further embodiments, the facial mask covers and matingly contacts at least 55% of the surface area of the face of the user, at least 65% of the surface area of the face of the user, and at least 75% of the surface area of the face of the user.

By extending the mask onto these surfaces, the present invention also allows for the mask to be constructed so that it does not touch the more sensitive parts of the user's face, including the nose 22 and the chin, especially the chin boss 30. The mask is designed and constructed to not touch the chin boss such that the user can move the chin while the mask is on. This mobility is found to reduce the irritation of wearing a mask.

Some masks of the prior art rely on a flexible peripheral seal around the edges of the mask to conform to the unique features of the user's face. In order to seal against the face of the user, the flexible peripheral seal becomes deformed due to the force from the face against the peripheral seal. Additionally or alternatively, the face of the user becomes deformed during wear of the mask due to the force from the peripheral seal against the face. Pressure is defined as force per unit area. The force of the mask caused by the straps holding the mask to the face of the user is distributed only across the perimeter contact portion, resulting in a high pressure against the face. This limited contact footprint of the flexible peripheral seal around the edges of a mask causes creases, lines, or other undesired cosmetic changes in the user's face upon continual use of the mask.

In contrast, the facial mask of the present invention does not rely on perimeter contact to seal against face. In fact, the force applied from the mask to the face or the force applied from the face to the mask around the edge or perimeter of the mask during use is less than or equal to the average of the entirety of the force applied from the mask to the face or the force applied from the face to the mask during use. The force applied from the mask to the face or the force applied from the face to the mask around the edge or perimeter of the mask is also less than or equal to the force applied from the mask to the face or the force applied from the face to the mask at any specific point or group of points of face/mask contact during use. This results in a substantially even pressure distribution across the contact area. Additionally, unlike much of the prior art, the mask of the present invention does not include a separate peripheral portion to seal around the edge of the mask/face interface because the mask of the present invention does not merely seal around the edge of the mask/face interface. Advantageously, the facial mask of the present invention matingly contacts at least 50% of the surface area of the face, which provides a larger surface area to sealingly contact the face. The mask configuration also provides for reduced pressure points and/or no pressure points on higher contour areas of the face (e.g., the nose, between the nose and the upper lip, the cheekbones, the jawline, the chin), and therefore provides for increased comfort to the user. For the higher contour areas of the face in contact with the mask (e.g., the cheekbones, the jawline), the pressure points are reduced due to the force of the mask on the face being distributed over a large surface area (e.g., at least 50% of the surface area of the face). Further, because the facial mask matingly contacts the face, neither the face nor the mask become deformed during wear of the mask, which prevents creases, lines, or other undesired cosmetic changes in the user's face.

Additionally, the facial mask matingly contacting the face allows for greater stability of the mask during the continuous use while sleeping. Users often move while sleeping, which can lead to leaks and a poor fit on the face. Advantageously, the facial mask of the present invention matingly contacts the face of the user and matches the facial contours of the individual user. This prevents the facial mask from shifting on the user's face while sleeping.

The facial mask preferably includes strap attachments and at least one strap 34 for securing the mask portion to the face. The at least one strap 34 is attached to the facial mask via strap attachment points 32. In a preferred embodiment, the strap attachment points 32 are positioned on opposite sides of the facial mask. In one embodiment, the strap attachment points 32 are loop holes. In one embodiment, the strap attachments consist of only two strap attachment points 32. The at least one strap 34 is sized to extend around the user's head. The at least one strap 34 is sized to not contact the ears of the individual user. In a preferred embodiment, the at least one strap 34 is sized to not contact the cheeks of the individual user.

In a preferred embodiment, the at least one strap 34 is a single axial strap. Advantageously, a single strap may be used with the present invention due to the substantial contact of the surface area of the face, including the forehead 12 and the cheeks 14 of the user. In contrast, prior art masks that contact the forehead of the user either require more than one strap or include the strap in a disadvantageous location (e.g., across the ears, the forehead, or the cheeks) that irritate the user. Including more than one strap is disadvantageous because it requires the user to fasten and unfasten at least two straps when putting on or removing the mask, as well as requiring contact between the straps and the user's head or face in multiple locations.

The at least one strap 34 is for applying a pressure distributed across the customized, contoured facial mask portion, wherein the pressure is distributed substantially uniformly across the contact portion of the customized, contoured facial mask portion. Substantially uniformly distributed pressure means that the pressure is distributed evenly (i.e., pressure exerted on the face by the mask is equal at every point of contact between the mask and the face), or alternatively, pressure is distributed across the mask such that pressure from the mask to the face at any point of contact between the mask and the face differs by only between about 0-10%, and more preferably between about 0-5%, from pressure from the mask to the face at any other point of contact between the mask and the face. Advantageously, the substantial mating contact of the face of the user by the mask, preferably at least 50% of the surface area, more preferably at least about 80% of the surface area, provides for reduced pressure points on higher contour areas of the face, and therefore provides increased comfort to the user.

In a preferred embodiment, the at least one strap 34 is adjustable to accommodate different head diameters. The at least one strap 34 may be formed of an elastic or inelastic material. In one embodiment, the at least one strap 34 is formed of rubber, silicone, or a foam. In another embodiment, the at least one strap 34 is covered with neoprene. In one embodiment, the at least one strap 34 is adjustable using at least one toggle, hook-and-loop tape, at least one snap, or at least one buckle (e.g., cam buckle, side release buckle). In yet another embodiment, a length and/or a width of the at least one strap 34 is determined based on a 3D scan of the user's head. The at least one strap 34 is adjustable or manufactured to a predetermined length and/or a predetermined width, which ensures proper fit of the sleep apnea mask when used in conjunction with the customized, contoured facial mask portion.

For increased oxygen intake and to facilitate breathing of the user to address issues of sleep apnea, the mask of the present invention further includes an airway passage 36 positioned in the nose region of the mask, and further including a breathing tube 38 connected to the mask at the airway passage 36, which extends outwardly from a nasal area of the contoured facial mask face surface portion. In one embodiment, the airway passage 36 and the breathing tube connector is molded into the facial mask. In another embodiment, the breathing tube is removably attachable to the mask (i.e., it is connectable and disconnectable) by a connection region that is matingly connectable. By way of example and not limitation, the connection region includes a threaded zone for rotational connection of the breathing tube with the airway passage.

Figure 2:
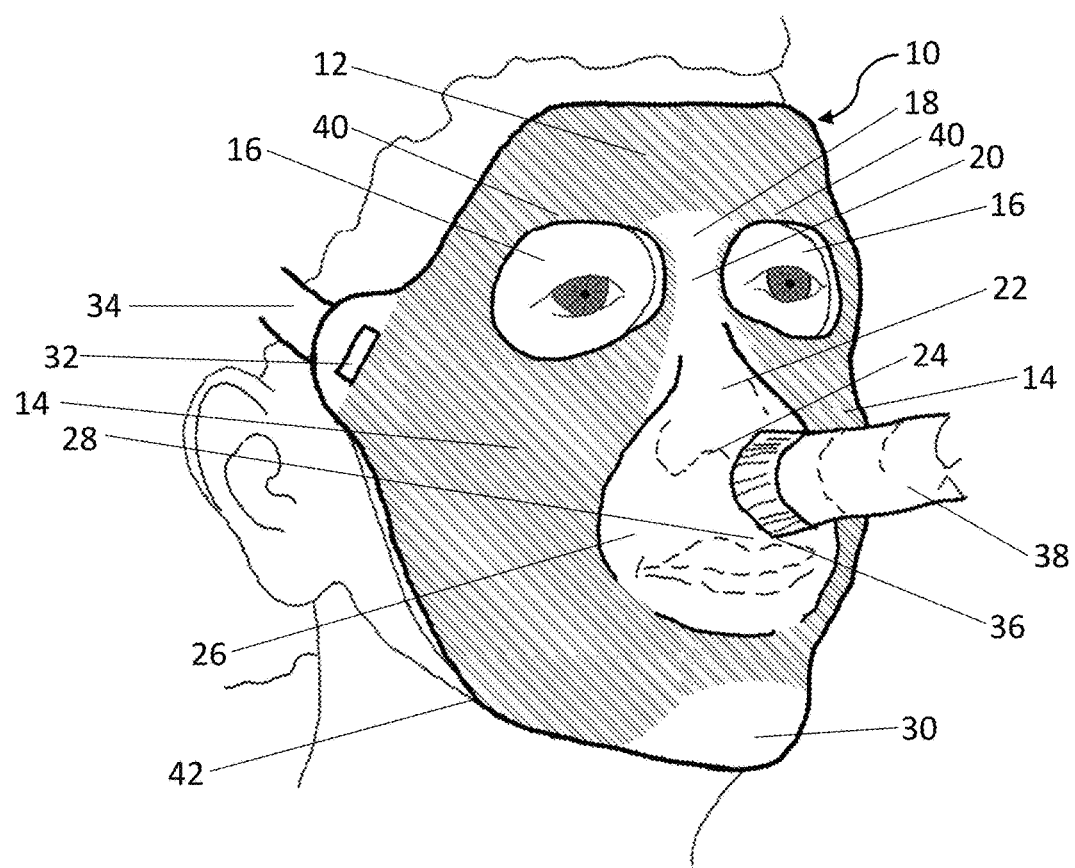
FIG. 2 is a schematic diagram of a perspective view of another embodiment of the invention.

FIG. 2 is a schematic diagram of a perspective view of another embodiment of the invention. In one embodiment, the contact area includes the jaw region 42. The facial mask 10 of FIG. 2 contacts a larger surface area of the face than the facial mask of FIG. 1. Specifically, the facial mask 10 of FIG. 2 a larger portion of the cheeks 14, a larger area under the mouth, and a portion of the jaw 42.

Figure 3:
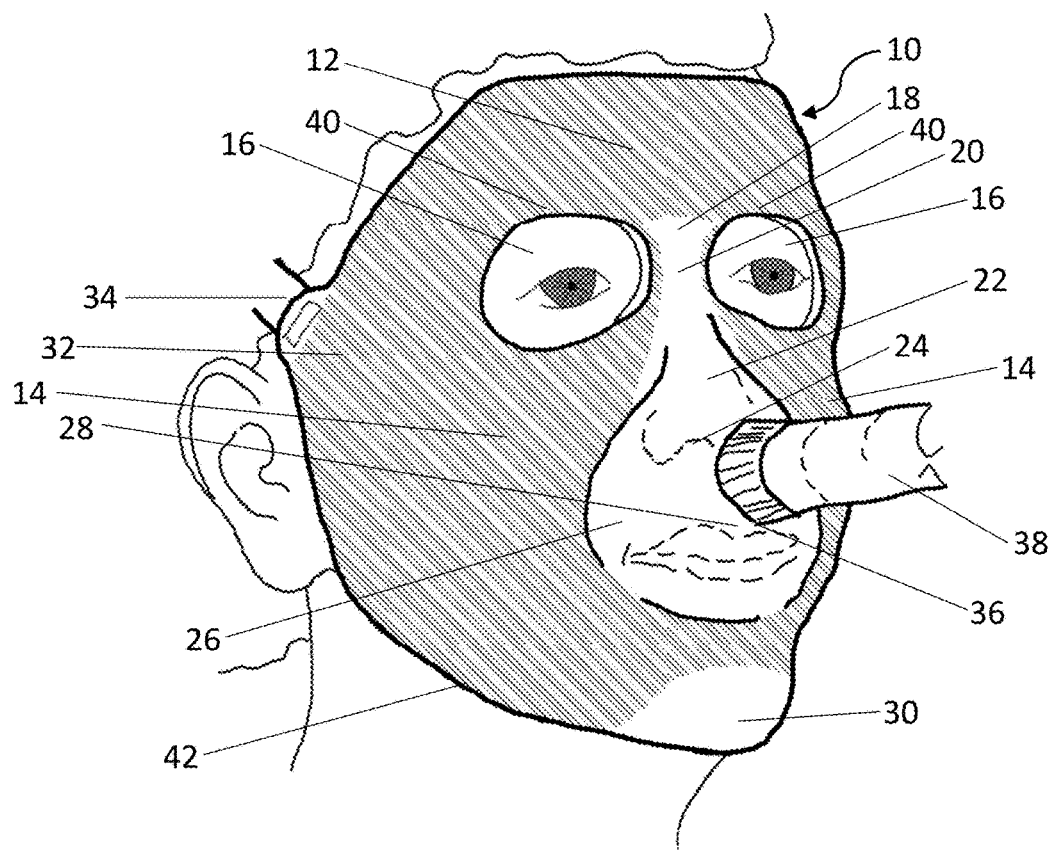
FIG. 3 is a schematic diagram of a perspective view of yet another embodiment of the invention.

FIG. 3 is a schematic diagram of a perspective view of yet another embodiment of the invention. The facial mask 10 of FIG. 3 contacts a larger surface area of the face than the facial mask of FIG. 2. Specifically, the facial mask 10 of FIG. 3 contacts a larger portion of the forehead 12 (i.e., is closer to the hairline), a larger portion of the cheeks 14, and a larger portion of the jaw 42.

Figure 4:
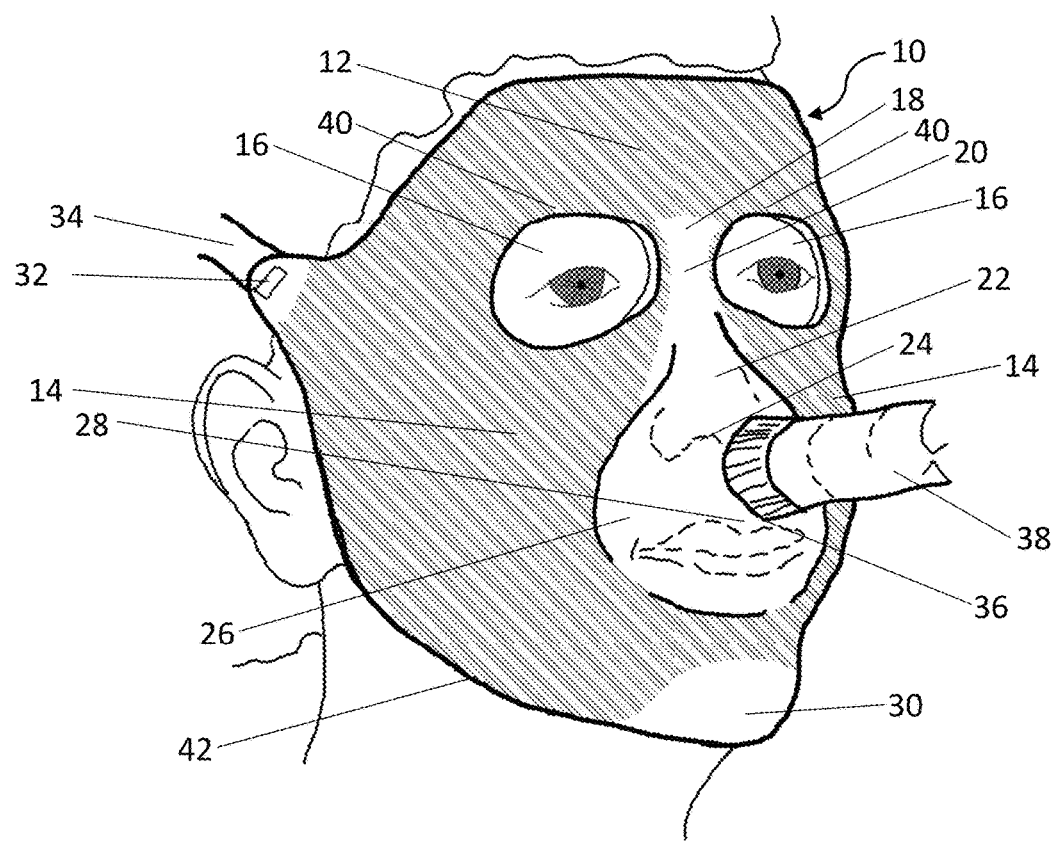
FIG. 4 is a schematic diagram of a perspective view of still another embodiment of the invention.

FIG. 4 is a schematic diagram of a perspective view of still another embodiment of the invention. In one embodiment, the facial mask connects with the strap at a position even with or behind the ear (i.e., even with or behind the tragus). In the embodiment shown in FIG. 4, the facial mask connects with the strap at a position above and behind the ear. The strap preferably connects to the strap attachment points on the mask above the ear, which positions the strap at an angle between about 45 degrees and about 75 degrees from a horizontal line that runs tangent to the top of the ear. The strap extends around the back of the user's head during use. This configuration of the strap helps ensure that the mask maintains mating contact with the face of the user during use. Advantageously, this configuration of the strap allows for a greater surface area of the face to be in mating contact with the facial mask.

The facial mask preferably has no sharp edges. Additionally, the facial mask has a uniform texture for the underside layer. Advantageously, the lack of sharp edges and the uniform texture aid in the prevention of lines, creases, and other cosmetic changes in the face.

Figure 5:
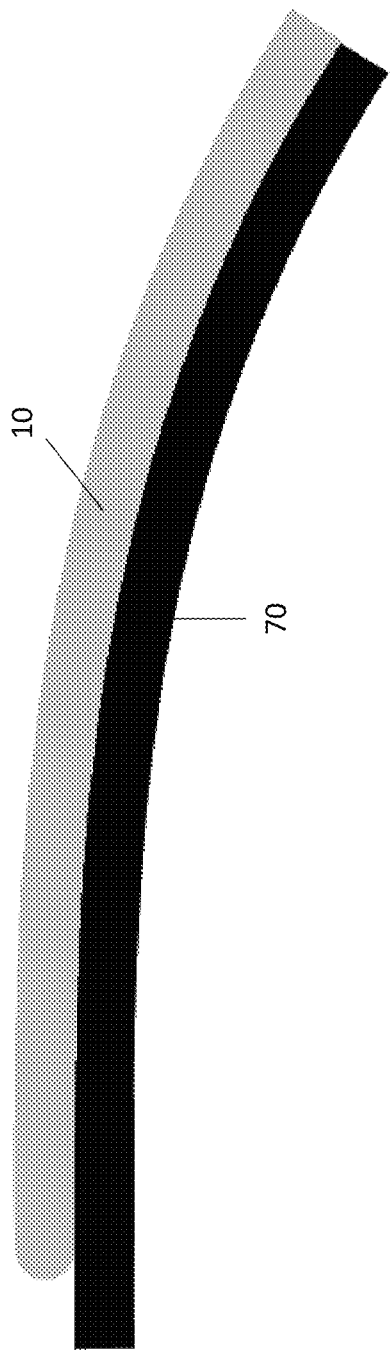
FIG. 5 illustrates a perspective view of one embodiment of a facial mask having a rounded edge.

In one embodiment, edges of the facial mask (e.g., around the perimeter of the mask, around the eyes) have a rounded edge. FIG. 5 illustrates a perspective view of one embodiment of a facial mask having a rounded edge. The facial mask 10 is shown in mating contact with the facial surface 70 of the individual user.

Figure 6:
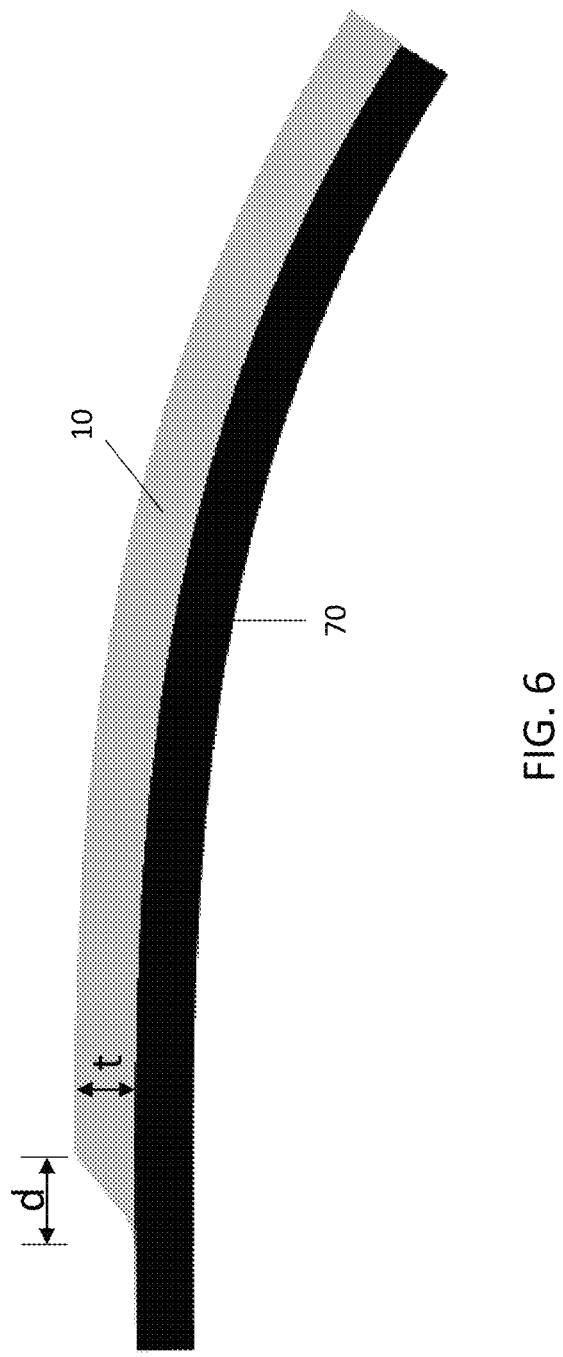
FIG. 6 is a schematic diagram of one embodiment of a facial mask having at least one zone with a graduated thickness.

In one embodiment, the facial mask has at least one zone with a graduated thickness. FIG. 6 is a schematic diagram of one embodiment of a facial mask having at least one zone with a graduated thickness. In a preferred embodiment, the facial mask 10 has a thickness t between about 0.0625 inches and about 0.1875 inches. In another embodiment, the facial mask 10 has a thickness t between about 0.0625 inches and about 0.25 inches. In one embodiment, the thickness t is graduated from 0% t to 100% t over a distance d. In a preferred embodiment, the distance d is less or equal to about 1 inch. In another embodiment, the distance d is less than or equal to about 0.75 inch, less than or equal to about 0.5 inch, less than or equal to about 0.25 inch, less than or equal to about 0.125 inch, or less than or equal to about 0.0625 inch. In the example shown in FIG. 6, the slope of the facial mask 10 in the zone of graduated thickness is substantially linear.

Figure 7:
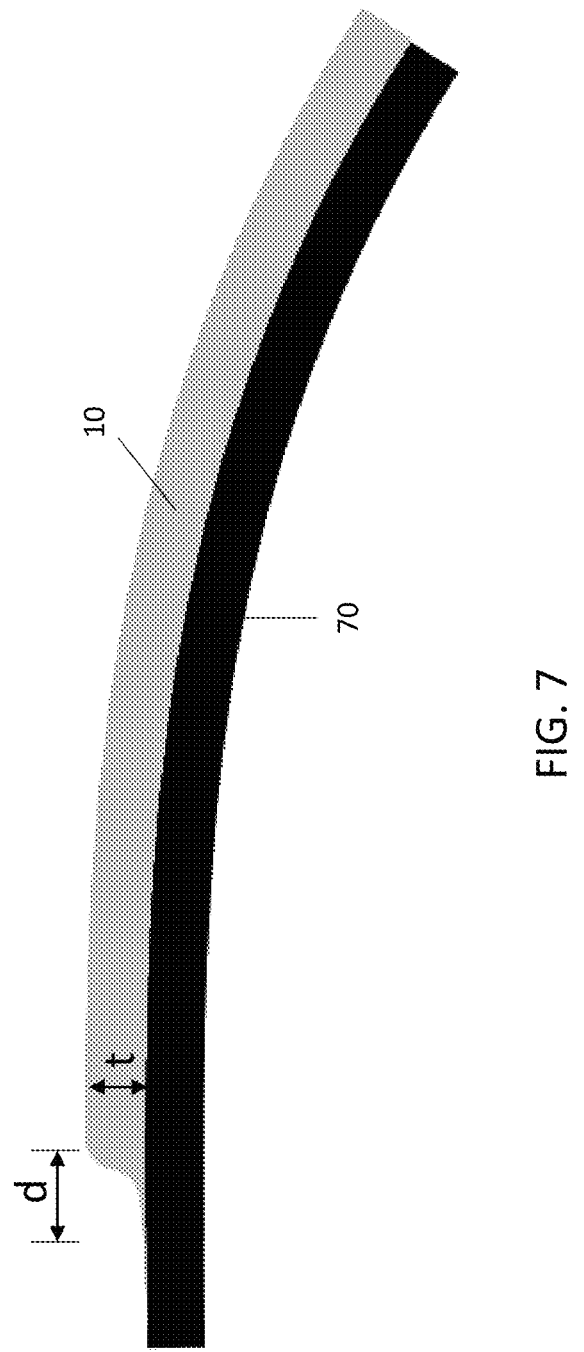
FIG. 7 is a schematic diagram of another embodiment of a facial mask having at least one zone with a graduated thickness.

Alternatively, the slope of the facial mask 10 in the zone of graduated thickness is non-linear, as shown in FIG. 7. Further, the distance d is slightly larger in the example shown in FIG. 7 than in the example shown in FIG. 6.

Figure 8:
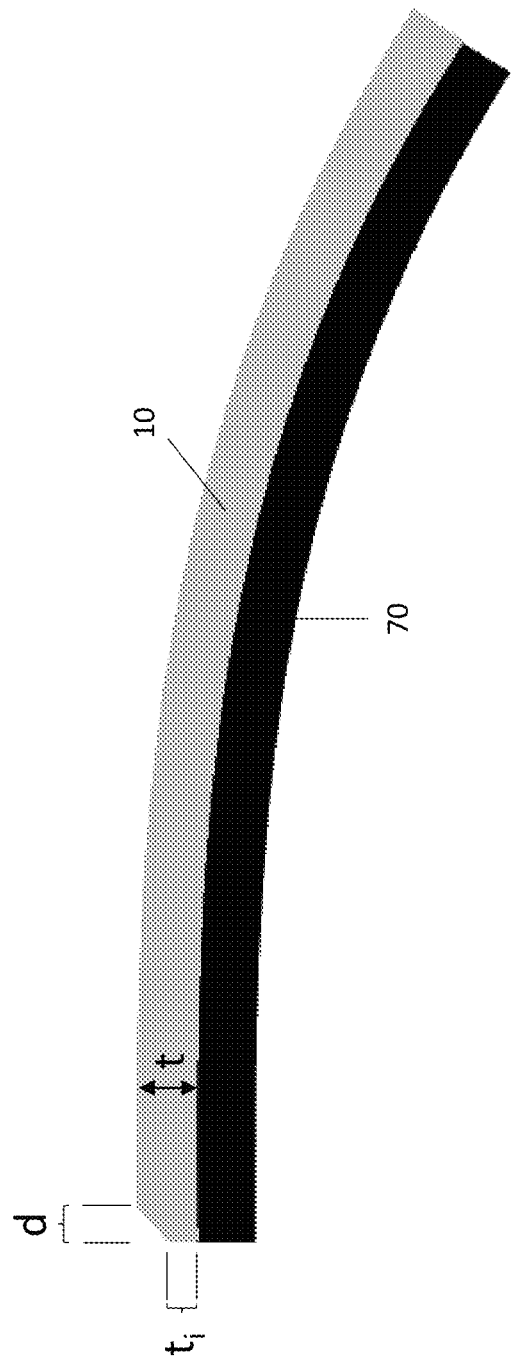
FIG. 8 is a schematic diagram of yet another embodiment of a facial mask having at least one zone with a graduated thickness.

In another embodiment, the thickness t is graduated from an initial thickness $t_i$ to the thickness t over a distance d. In the example shown in FIG. 8, the slope of the facial mask 10 in the zone of graduated thickness is substantially linear. In one embodiment, the initial thickness $t_i$ is equal to about 10%, about 20%, about 25%, about 30%, about 40%, about 50%, about 60%, about 70%, about 75%, about 80%, or about 90% of the thickness. Further, the edges are not rounded in the example shown in FIG. 8.

As previously described, pressure is distributed across the mask such that pressure from the mask to the face at any point of contact between the mask and the face differs by only between about 0-10%, and more preferably between about 0-5%, from pressure from the mask to the face at any other point of contact between the mask and the face. In one embodiment, the facial mask has at least one zone of graduated pressure. In a preferred embodiment, the at least one zone of graduated pressure is located at an edge of a contact region (e.g., around the eyes, around the periphery of the mask, around the nasal area). In another embodiment, the at least one zone of graduated pressure is located at a high contour area of the face (e.g., the cheekbones, the supraorbital ridges, the jawline). Advantageously, this embodiment decreases the pressure on the high contour area of the face, which increases the comfort to the user.

Figure 9:
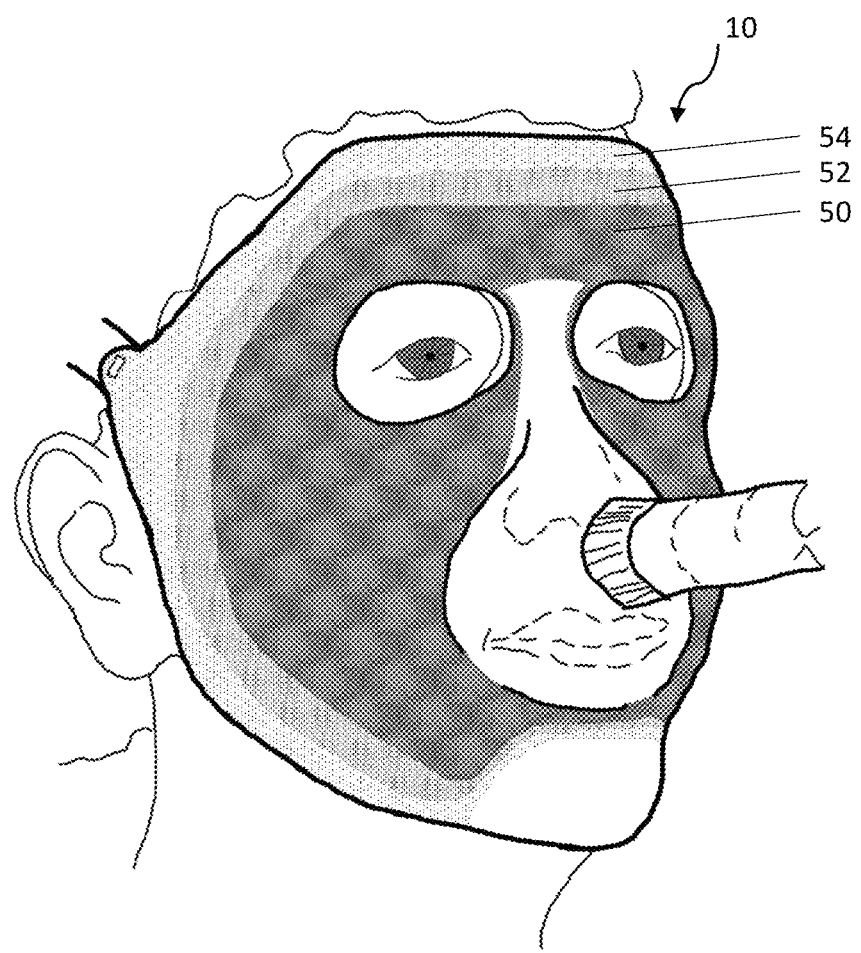
FIG. 9 is a schematic diagram of a perspective view of one embodiment of the invention having two zones of graduated pressure.

FIG. 9 is a schematic diagram of a perspective view of one embodiment of the invention having two zones of graduated pressure. In one embodiment, zones 52 and 54 are graduated pressure zones each having a pressure equal to less than 100% of the pressure in zone 50. In one example, zone 52 has a pressure equal to about 97.5% of the pressure in zone 50 and zone 54 has a pressure equal to about 95% of the pressure in zone 50. In another example, zone 52 has a pressure equal to about 95% of the pressure in zone 50 and zone 54 has a pressure equal to about 90% of the pressure in zone 50. Advantageously, the graduated pressure zone distributes the load to minimize the pressure from the edge of the mask contacting the face of the user during use, as edge contact from the mask to the face of the user may create lines, wrinkles, or other undesired cosmetic changes.

Figure 10:
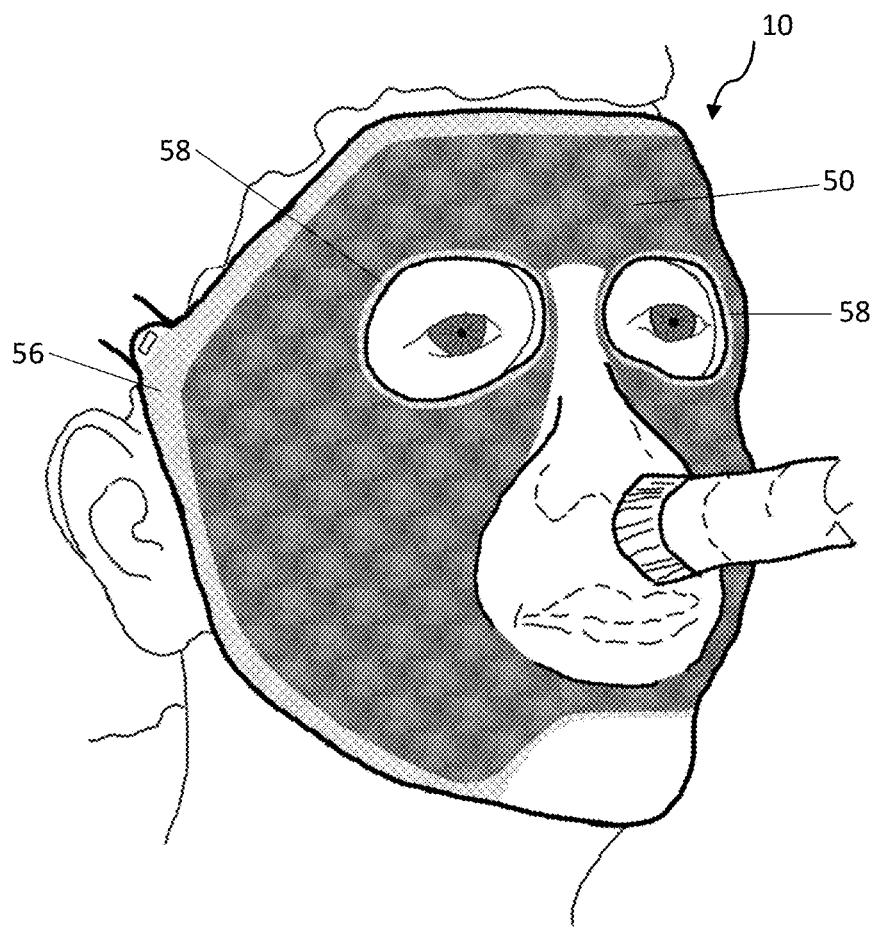
FIG. 10 is a schematic diagram of a perspective view of another embodiment of the invention having two zones of graduated pressure.

FIG. 10 is a schematic diagram of a perspective view of another embodiment of the invention having two zones of graduated pressure. In one embodiment, zones 56 and 58 are graduated pressure zones each having a pressure equal to less than 100% of the pressure in zone 50. In this example, zone 58 is located around each eye and zone 56 is located around the perimeter of the mask. In one example, zones 56 and 58 have equal pressures. For example, zones 56 and 58 have a pressure equal to about 95% of the pressure in zone 50. In other examples, zones 56 and 58 have a pressure equal to about 97.5%, about 92.5%, or about 90% of the pressure in zone 50.

Alternatively, zones 56 and 58 do not have equal pressures. For example, zone 56 has a pressure equal to about 95% of the pressure in zone 50 and zone 58 has a pressure equal to about 97.5% of the pressure in zone 50. In another example, zone 56 has a pressure equal to about 97.5% of the pressure in zone 50 and zone 58 has a pressure equal to about 95% of the pressure in zone 50. In other embodiments, zone 56 has a pressure equal to about 97.5%, about 95%, about 92.5%, or about 90% of the pressure in zone 50 and zone 58 has a pressure equal to about 97.5%, about 95%, about 92.5%, or about 90% of the pressure in zone 50.

Figure 11:
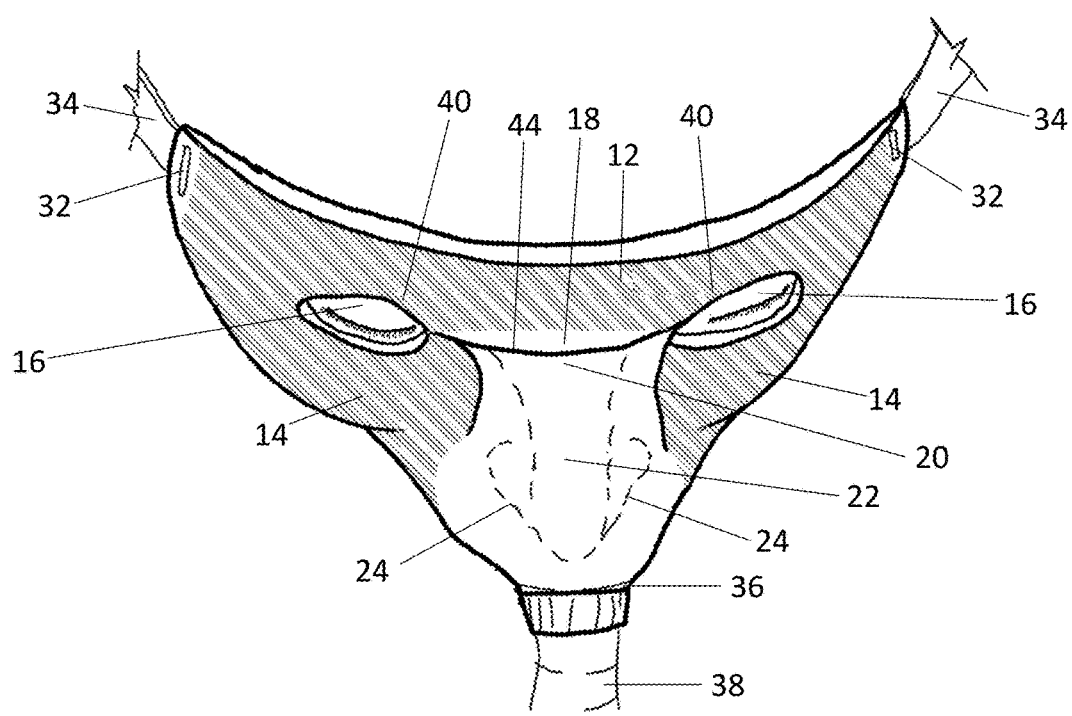
FIG. 11 is a schematic diagram of a top view of an embodiment of the invention.

FIG. 11 is a schematic diagram of a top view of an embodiment of the invention. The facial mask 10 preferably includes an outward curvature between the supraorbital ridges 40 to prevent the facial mask 10 from contacting the glabella 18.

Figure 12:
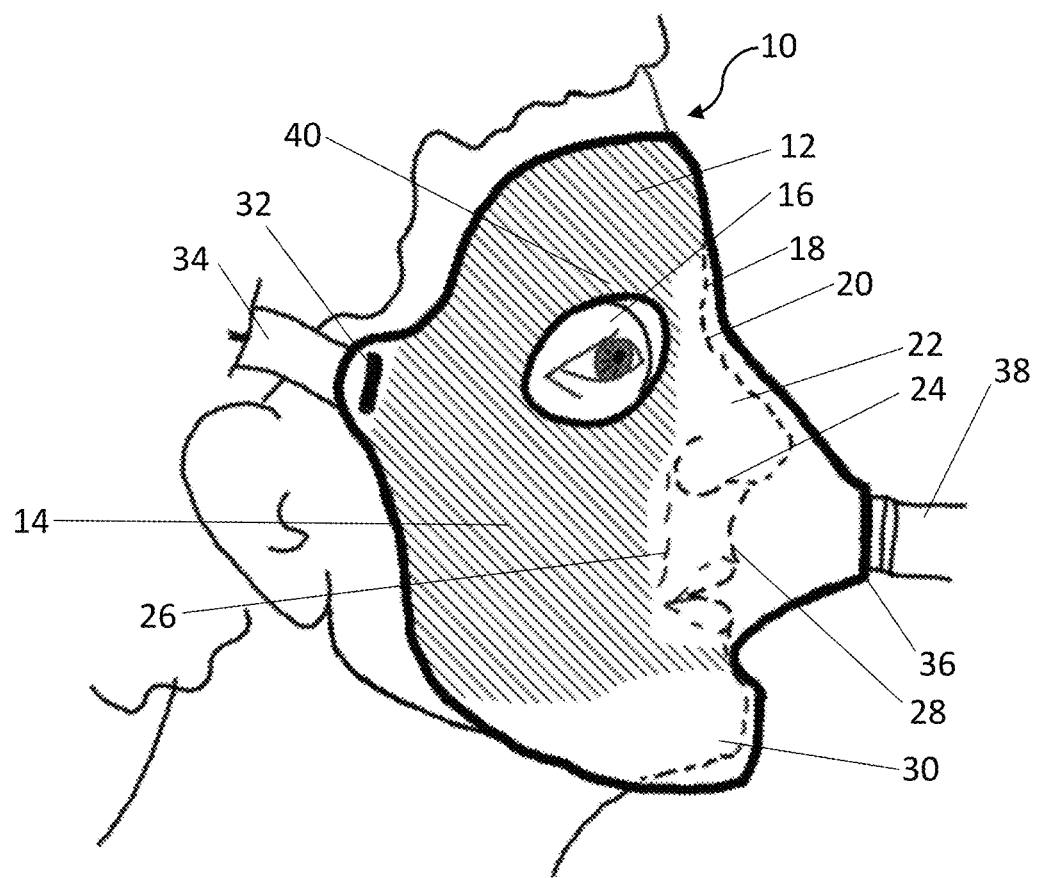
FIG. 12 is a schematic diagram of a side view of an embodiment of the invention.

FIG. 12 is a schematic diagram of a side view of an embodiment of the invention. As previously described, the facial mask preferably does not contact the glabella 18, the root of the nose 20, the nose 22, the nostrils 24, the nasolabial folds (i.e., "smile lines" or "laugh lines") 26, the philtrum 28, or the chin boss 30 of the user. In a preferred embodiment, the facial mask extends slightly under the chin of the user, wherein a clearance of between about ⅛ inch to about ¼ inch is provided. Alternatively, the clearance is between about ¼ inch and about ½ inch. In another embodiment, the clearance is between about ½ inch and about ¾ inch. In yet another embodiment, the clearance is between about ¾ inch and 1 inch. In other embodiments, the clearance is any measurement between ¼ inch and 1 inch. This clearance provides for chin mobility while wearing the facial mask, which increases the comfort to the user while wearing the mask.

Masks of the prior art do not extend across the forehead and beneath the chin, but rather are in contact with and supported by the glabella, root of the nose, areas directly below the nose (e.g., the philtrum and nasolabial furrows), and/or the chin. Thus, the prior art teaches both the more sensitive parts of the face supporting the mask (e.g., the glabella, philtrum, chin boss) and a smaller area of the face supporting the mask. Advantageously, the present invention teaches a larger support area and less-sensitive parts of the face as support areas.

Figure 13:
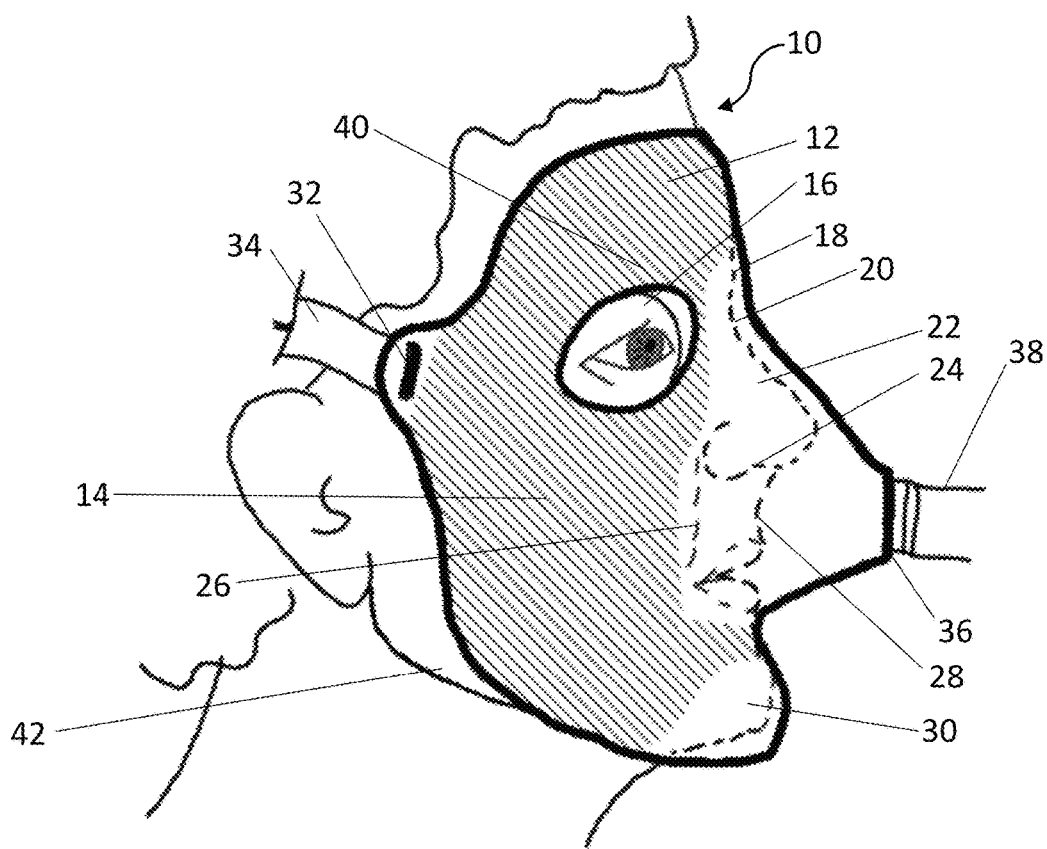
FIG. 13 is a schematic diagram of a side view of another embodiment of the invention.

FIG. 13 is a schematic diagram of a side view of another embodiment of the invention. The facial mask 10 of FIG. 13 contacts a larger surface area of the face than the facial mask of FIG. 12. Specifically, the facial mask 10 of FIG. 13 contacts a larger portion of the cheeks 14, a larger area under the mouth, and a portion of the jaw 42.

Figure 14:
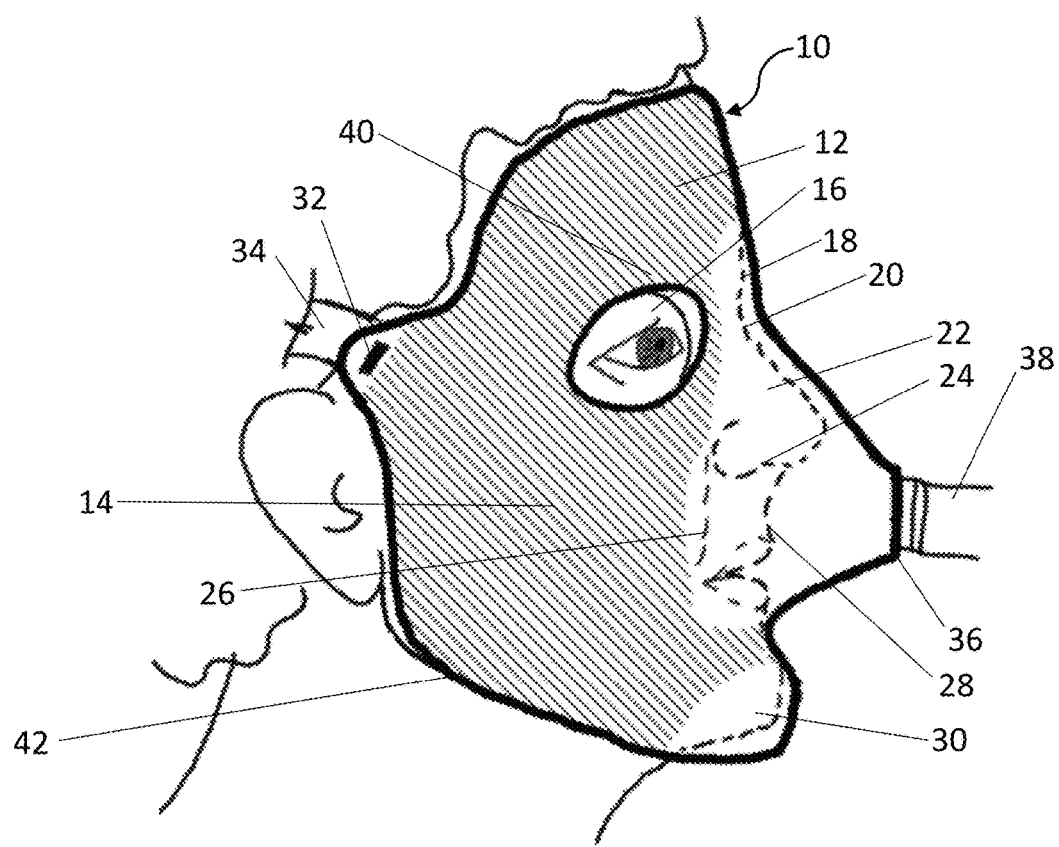
FIG. 14 is a schematic diagram of a side view of yet another embodiment of the invention.

FIG. 14 is a schematic diagram of a side view of yet another embodiment of the invention. The facial mask 10 of FIG. 14 contacts a larger surface area of the face than the facial mask of FIG. 13. Specifically, the facial mask 10 of FIG. 14 contacts a larger portion of the forehead 12 (i.e., is closer to the hairline), a larger portion of the cheeks 14, and a larger portion of the jaw 42.

Figure 15:
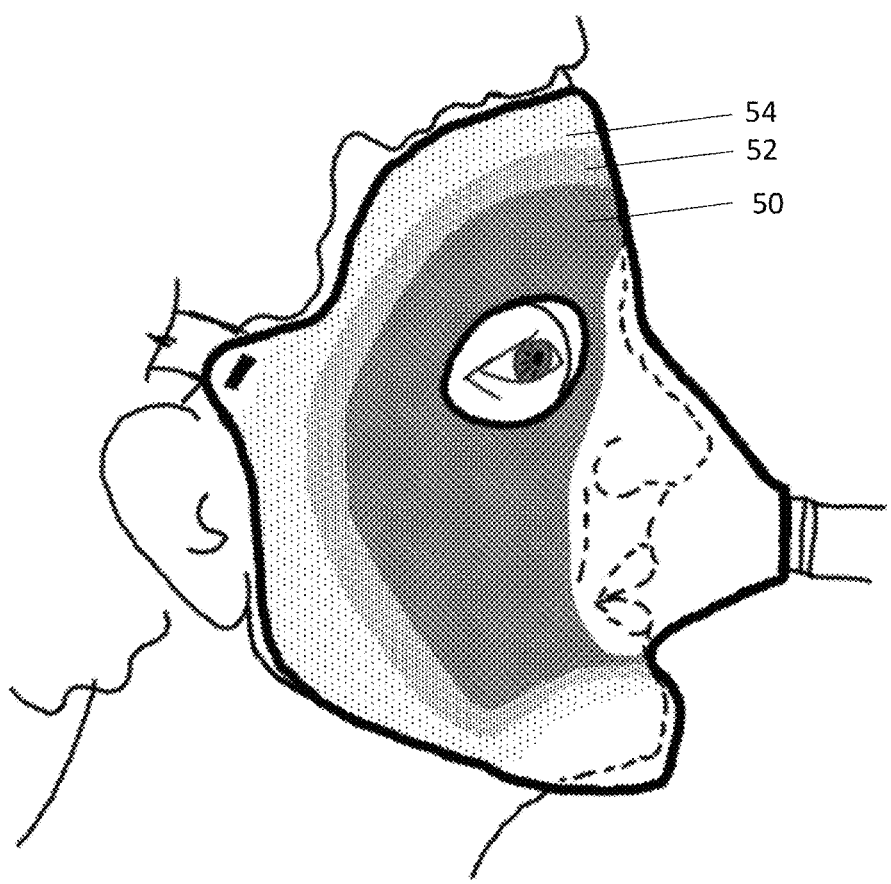
FIG. 15 is a schematic diagram of a side view of an embodiment of the invention shown in FIG. 9.

FIG. 15 is a schematic diagram of a side view of an embodiment of the invention shown in FIG. 9. In FIG. 15, the facial mask has two zones of graduated pressure. In one embodiment, zones 52 and 54 are graduated pressure zones each having a pressure equal to less than 100% of the pressure in zone 50. In one example, zone 52 has a pressure equal to about 97.5% of the pressure in zone 50 and zone 54 has a pressure equal to about 95% of the pressure in zone 50. In another example, zone 52 has a pressure equal to about 95% of the pressure in zone 50 and zone 54 has a pressure equal to about 90% of the pressure in zone 50. Advantageously, the graduated pressure zone distributes the load to minimize the pressure from the edge of the mask contacting the face of the user during use, as edge contact from the mask to the face of the user may create lines, wrinkles, or other undesired cosmetic changes.

In a preferred embodiment, the facial mask includes ventilation holes to provide additional comfort to the user. In one embodiment, the ventilation holes are 0.1 mm to 2.5 mm in diameter. In another embodiment, the ventilation holes are convergent such that the entrance holes are greater in diameter than the exit holes. In one embodiment, the ventilation holes have an entrance diameter of 2.4 mm and an exit diameter of 0.8 mm. In a preferred embodiment, the facial mask includes 40-50 ventilation holes.

Figure 16:
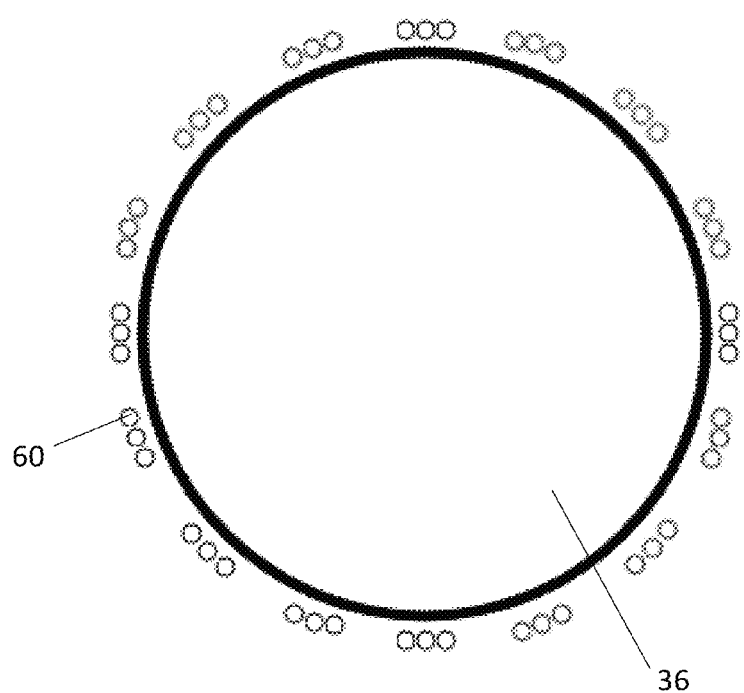
FIG. 16 illustrates ventilation holes according to one embodiment of the invention.

FIG. 16 illustrates ventilation holes according to one embodiment of the invention. In this embodiment, the ventilation holes are concentric around the airway passage 36. Although this embodiment is shown as concentric around the airway passage, this configuration can be molded into other connective pieces between the device and mask (e.g., an elbow, a frame, a tube). Additionally, this embodiment is shown in a circular path concentric around the airway passage, but other shapes (e.g., triangular, rectangular) are possible.

The ventilation holes preferably are slanted to optimize air flow. In one embodiment, the ventilation holes are angled about 30° to about 60° with respect to the surface. More preferably, the ventilation holes are angled about 45° with respect to the surface. In a preferred embodiment, the ventilation holes are unitarily formed into the mask through the 3D printing process.

Figure 17:
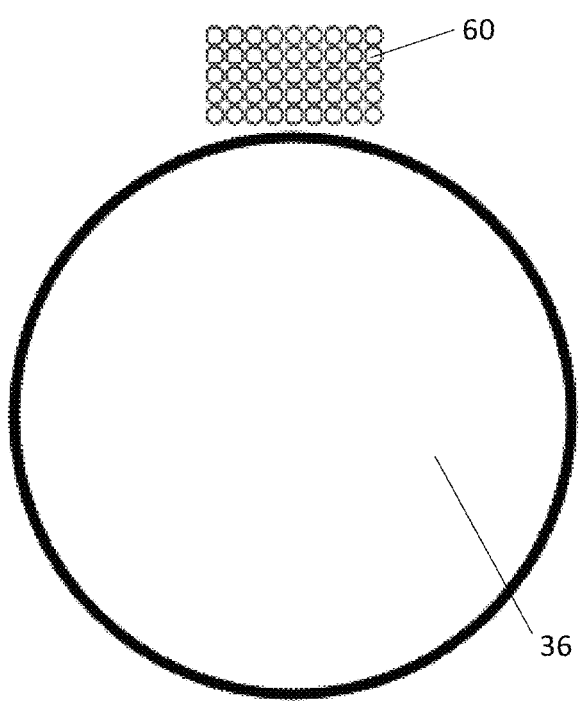
FIG. 17 illustrates ventilation holes according to another embodiment of the invention.

FIG. 17 illustrates ventilation holes according to another embodiment of the invention. In this embodiment, the ventilation holes are positioned above the airway passage 36. The ventilation holes preferably are slanted to move exhaled gases away from the user's face.

Figure 18:
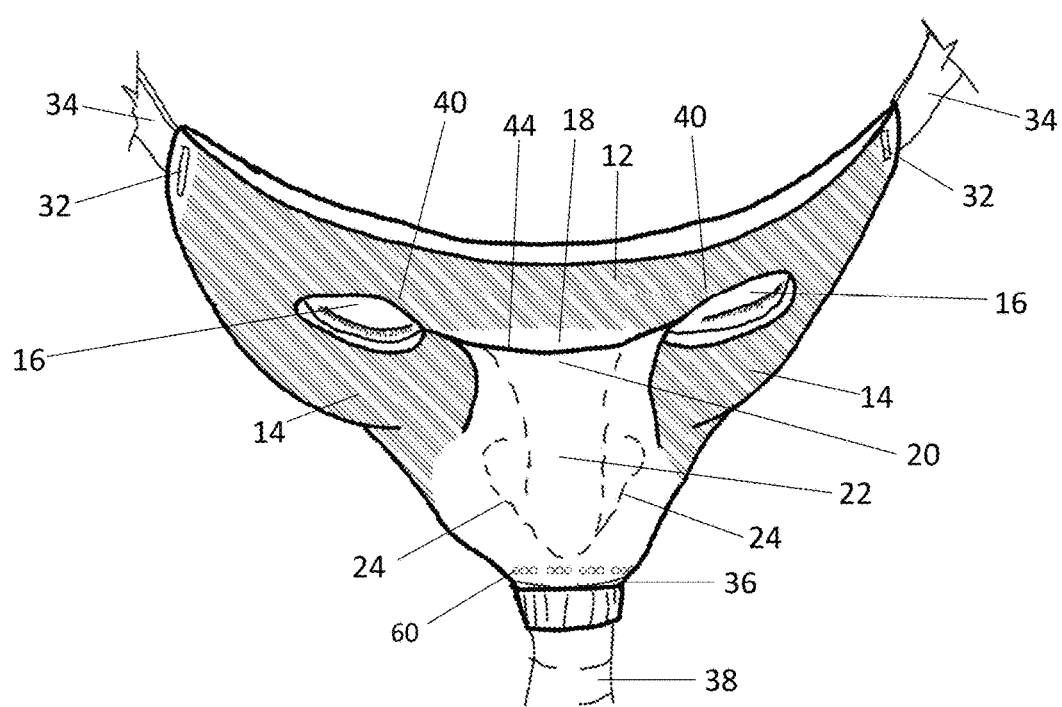
FIG. 18 is a schematic diagram of a top view of an embodiment of the invention with ventilation holes.

FIG. 18 is a schematic diagram of a top view of an embodiment of the invention with ventilation holes 60.

Figure 19:
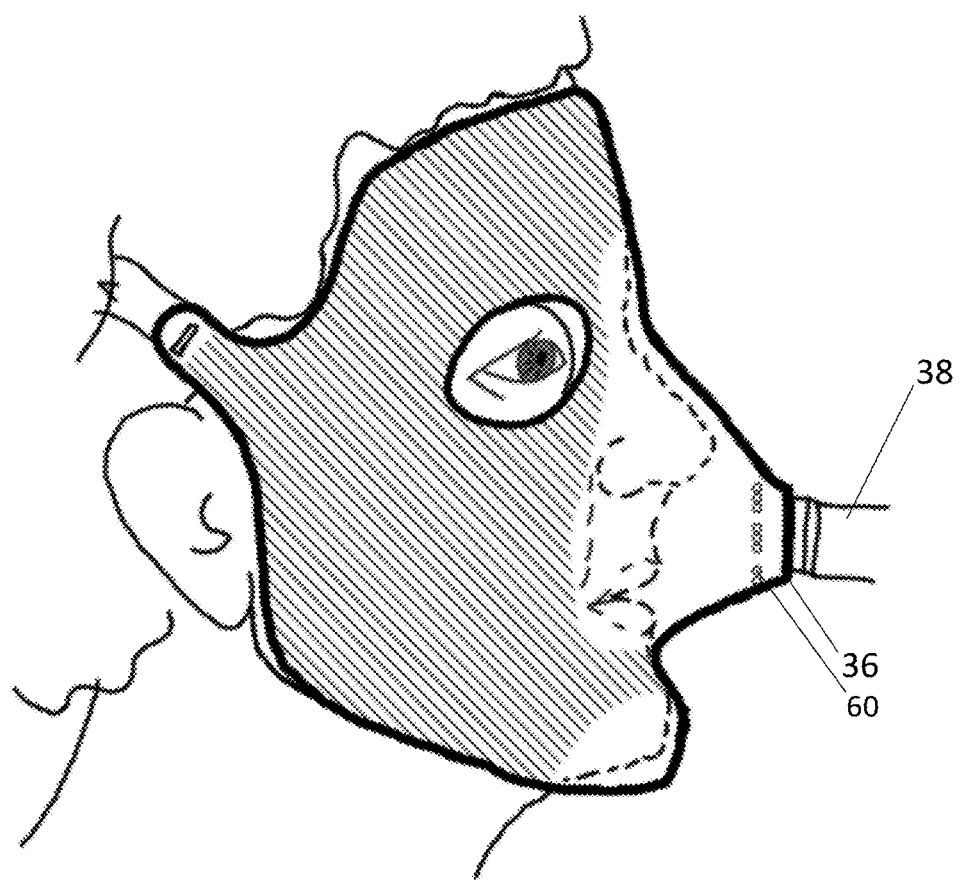
FIG. 19 is a schematic diagram of a side view of an embodiment of the invention with ventilation holes.

FIG. 19 is a schematic diagram of a side view of an embodiment of the invention with ventilation holes 60.

Figure 20:
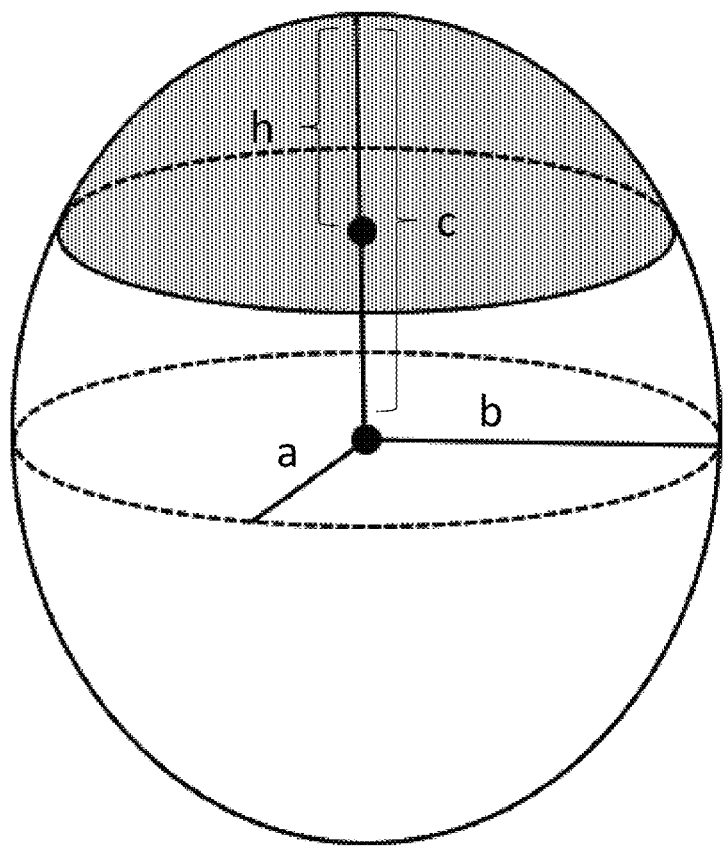
FIG. 20 illustrates a half-ellipsoid with axes a, b, and c, and a height h of an ellipsoid cap.

As previously described, the facial mask of the present invention matingly contacts at least 50% of the surface area of the face. The term "surface area" as used in this application means the total area of the outside layer of a three-dimensional object (e.g., the face). An article, "A geometric model of defensive peripersonal space" by authors Bufacchi et al. in the *Journal of Neurophysiology*, estimates the face as a half-ellipsoid with axes equal to 11.3 cm, 7.4 cm, and 9.8 cm. FIG. 20 illustrates a half-ellipsoid with axes a, b, and c, and a height h of an ellipsoid cap, which appears as a dotted region on the figure. The surface area of the half-ellipsoid is equal to 564.3 cm$^2$ (87.5 in$^2$). Using values for h=9.8 cm (equivalent to 100% surface area of face), h=7.9 cm (equivalent to 80% surface area of face), h=5.02 cm (equivalent to 50% surface area of face), and h=2.05 cm (equivalent to 20% surface area of face), three-dimensional models were generated using SOLIDWORKS, a computer-aided design program.

Figure 21:
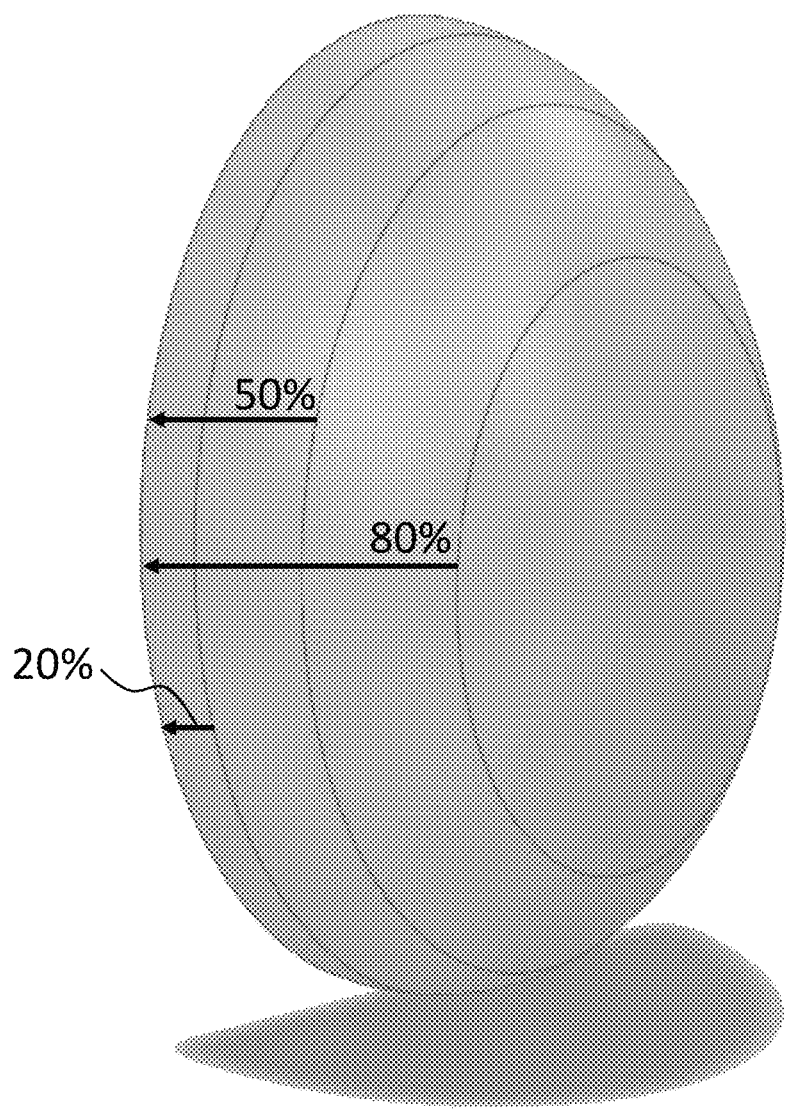
FIG. 21 shows an angled perspective view of the half-ellipsoid with 20% of the surface area, 50% of the surface area, and 80% of the surface area of the half-ellipsoid labeled.

FIG. 21 shows an angled perspective view of the half-ellipsoid with 20% of the surface area, 50% of the surface area, and 80% of the surface area of the half-ellipsoid labeled. As the eyes and mouth are the center of the face, partial surface areas are determined from the periphery of the face toward the center of the face.

Figure 22:
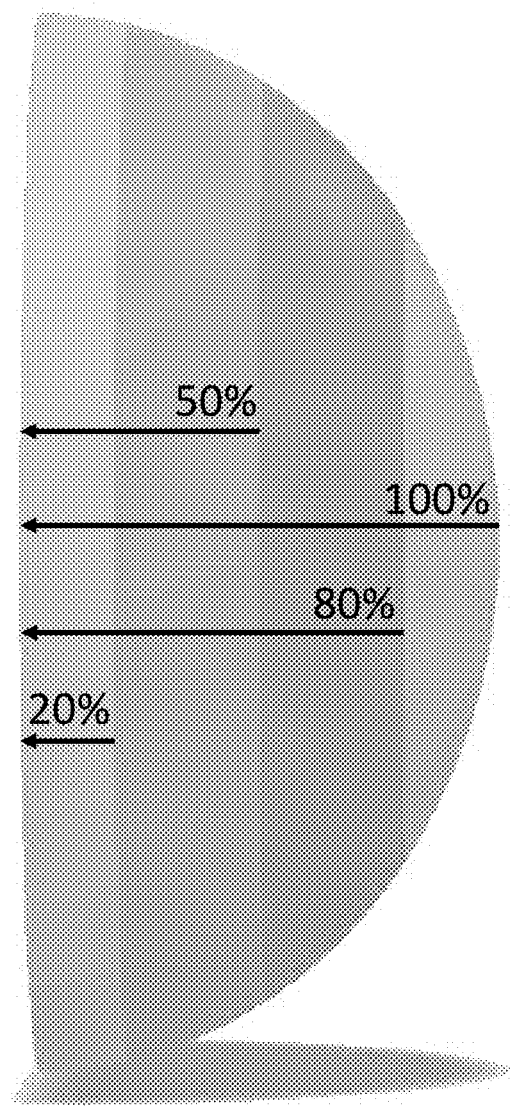
FIG. 22 shows a side perspective view of the half-ellipsoid with 20% of the surface area, 50% of the surface area, 80% of the surface area, and 100% of the surface area of the half-ellipsoid labeled.

FIG. 22 shows a side perspective view of the half-ellipsoid with 20% of the surface area, 50% of the surface area, 80% of the surface area, and 100% of the surface area of the half-ellipsoid labeled. Again, as the eyes and mouth are the center of the face, partial surface areas are determined from the periphery of the face toward the center of the face.

Certain modifications and improvements will occur to those skilled in the art upon a reading of the foregoing description. By way of example, the customized facial contour mask of the present invention may be adapted for use with cosmetic treatments, in particular for time-release or extended-release of beneficial chemicals or topical applications to the face, especially to substantially the entire face surface (excluding the eyes, mouth, and nasal breathing passages). In alternative embodiments, they may be adapted for use for pilots or firemen, or for the military, for extended-wear oxygen masks or gas masks that provide increased comfort, wherein the masks are customized to the user's facial contours. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. A facial mask for addressing sleep apnea in an individual user, comprising a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use;

wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user;

wherein the customized, contoured facial mask portion is adapted to extend below a chin of the individual user during use;

wherein the contact portion is configured to not contact a chin boss of the individual user during use;

wherein the contact portion is configured to not contact a nose of the individual user during use;

wherein the contact portion is configured to not contact a philtrum of the individual user during use;

wherein the contact portion is configured to not contact a glabella of the individual user during use;

wherein the contact portion is configured to seal around eyes of the individual user during use;

wherein the contact portion is adapted to substantially contact a forehead of the individual user during use;

wherein the contact portion is adapted to substantially contact cheeks of the individual user during use;

wherein the facial mask is configured to cover the glabella of the individual user during use;

wherein the facial mask is configured to not cover and not contact the eyes of the individual user during use; and wherein the at least one strap is sized to extend around the user's head and is for applying a pressure distributed across the customized, contoured facial mask portion.

2. The facial mask of claim 1, wherein the pressure is distributed substantially uniformly across the customized, contoured facial mask portion that contacts the face of the individual user.

3. The facial mask of claim 1, wherein the customized, contoured facial mask portion is sized to matingly contact at least 50% of the surface area of the face of the individual user.

4. The facial mask of claim 1, wherein the customized, contoured facial mask portion is sized to matingly contact at least 80% of the surface area of the face of the individual user.

5. The facial mask of claim 1, wherein the contact portion is configured to contact supraorbital ridges of the individual user during use.

6. The facial mask of claim 1, wherein the contact portion is configured to not contact nasolabial furrows of the individual user during use.

7. The facial mask of claim 1, wherein the customized, contoured facial mask portion is configured to substantially cover a nose of the individual user during use.

8. The facial mask of claim 1, wherein a clearance of between about 3.175 mm (⅛ inch) and about 6.35 mm (¼ inch) is provided below the chin of the individual user during use.

9. The facial mask of claim 1, wherein the strap attachments consist of only two strap attachment points, wherein the two strap attachment points are positioned on opposite sides of the facial mask.

10. The facial mask of claim 1, wherein the at least one strap is a single axial strap.

11. The facial mask of claim 1, wherein the contact portion includes at least one zone with a graduated thickness.

12. The facial mask of claim 1, wherein the facial mask is adapted for use with time-release or extended-release of topical applications to the surface area of the face of the individual user.

13. The facial mask of claim 1, further including a breathing tube extending outwardly from a nasal area of the customized, contoured facial mask portion.

14. The facial mask of claim 13, wherein the breathing tube is removably connectable to the customized, contoured facial mask portion via a connection region.

15. The facial mask of claim 14, wherein the connection region includes a threaded zone for rotational connection of the breathing tube with the customized, contoured facial mask portion.

16. A facial mask for addressing sleep apnea in an individual user, comprising a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use;
wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user;
wherein the customized, contoured facial mask portion is adapted to extend below a chin of the individual user during use;
wherein the contact portion is configured to not contact a chin boss of the individual user during use;
wherein the contact portion is configured to not contact a nose of the individual user during use;
wherein the contact portion is configured to not contact a philtrum of the individual user during use;
wherein the contact portion is configured to not contact a glabella of the individual user during use;
wherein the contact portion is configured to seal around eyes of the individual user during use;
wherein the contact portion is adapted to substantially contact a forehead of the individual user during use;
wherein the contact portion is adapted to substantially contact cheeks of the individual user during use;
wherein the facial mask is configured to cover the glabella of the individual user during use;
wherein the customized, contoured facial mask portion is sized to matingly contact at least 50% of the surface area of the face of the individual user; and
wherein the facial mask is configured to not cover and not contact the eyes of the individual user during use;
wherein the at least one strap is sized to extend around the user's head and is for applying a pressure distributed across the customized, contoured facial mask portion.

17. The facial mask of claim 16, wherein the contact portion includes at least one zone of graduated thickness.

18. A facial mask for addressing sleep apnea in an individual user, comprising a customized, contoured facial mask portion constructed and configured to matingly cover a corresponding contoured surface area of a face of the individual user and match facial contours of the face of the individual user, further including strap attachments and at least one strap for securing the customized, contoured facial mask portion to the face of the individual user during use;
wherein the customized, contoured facial mask portion includes a contact portion for matingly contacting the face of the individual user during use, wherein the contact portion is formed based on a three-dimensional (3-D) scan of the face of the individual user, and the contact portion is adapted to conform to unique facial features and match the facial contours of the individual user;
wherein the customized, contoured facial mask portion is adapted to extend below a chin of the individual user during use;
wherein the contact portion is configured to not contact a chin boss of the individual user during use;
wherein the contact portion is configured to not contact a nose of the individual user during use;
wherein the contact portion is configured to not contact a philtrum of the individual user during use;
wherein the contact portion is configured to not contact a glabella of the individual user during use;
wherein the contact portion is configured to seal around eyes of the individual user during use;
wherein the contact portion is adapted to substantially contact a forehead of the individual user during use;
wherein the contact portion is adapted to substantially contact cheeks of the individual user during use;
wherein the contact portion is adapted to contact supraorbital ridges of the individual user during use;
wherein the facial mask is configured to cover the glabella of the individual user during use;
wherein the customized, contoured facial mask portion is sized to matingly contact at least 80% of the surface area of the face of the individual user;
wherein the facial mask is configured to not cover and not contact the eyes of the individual user during use; and
wherein the at least one strap is sized to extend around the user's head and is for applying a pressure distributed across the customized, contoured facial mask portion.

\* \* \* \* \*